United States Patent
Gupta

(10) Patent No.: US 10,583,110 B2
(45) Date of Patent: Mar. 10, 2020

(54) ANTITUMORAL USE OF CABAZITAXEL

(71) Applicant: Aventis Pharma S.A., Antony (FR)

(72) Inventor: Sunil Gupta, Lexington, MA (US)

(73) Assignee: SANOFI MATURE IP, Paris (FR)

( * ) Notice: Subject to any disclaimer, the term of this patent is extended or adjusted under 35 U.S.C. 154(b) by 0 days.

(21) Appl. No.: 15/627,962

(22) Filed: Jun. 20, 2017

(65) Prior Publication Data

US 2018/0125810 A1    May 10, 2018

Related U.S. Application Data

(63) Continuation of application No. 14/575,566, filed on Dec. 18, 2014, now abandoned, which is a continuation of application No. 13/456,720, filed on Apr. 26, 2012, now Pat. No. 8,927,592, which is a continuation of application No. PCT/IB2010/054866, filed on Oct. 27, 2010.

(60) Provisional application No. 61/389,969, filed on Oct. 5, 2010, provisional application No. 61/383,933, filed on Sep. 17, 2010, provisional application No. 61/369,929, filed on Aug. 2, 2010, provisional application No. 61/355,888, filed on Jun. 17, 2010, provisional application No. 61/355,834, filed on Jun. 17, 2010, provisional application No. 61/293,903, filed on Jan. 11, 2010, provisional application No. 61/256,160, filed on Oct. 29, 2009.

(51) Int. Cl.
  *A61K 31/337* (2006.01)
  *A61K 31/164* (2006.01)
  *A61K 31/56* (2006.01)
  *A61K 31/573* (2006.01)
  *A61K 45/06* (2006.01)
  *A61K 38/19* (2006.01)

(52) U.S. Cl.
  CPC .......... *A61K 31/337* (2013.01); *A61K 31/164* (2013.01); *A61K 31/56* (2013.01); *A61K 31/573* (2013.01); *A61K 38/193* (2013.01); *A61K 45/06* (2013.01)

(58) Field of Classification Search
  CPC . A61K 31/337; A61K 31/573; A61K 31/4402
  See application file for complete search history.

(56) References Cited

U.S. PATENT DOCUMENTS

| | | |
|---|---|---|
| 4,814,470 A | 3/1989 | Colin et al. |
| 5,005,588 A | 4/1991 | Rubin |
| 5,438,072 A | 8/1995 | Bobee et al. |
| 5,698,582 A | 12/1997 | Bastart et al. |
| 5,714,512 A | 2/1998 | Bastart et al. |
| 5,750,561 A | 5/1998 | Bastart et al. |
| 5,847,170 A | 12/1998 | Bouchard et al. |
| 5,889,043 A | 3/1999 | Bouchard et al. |
| 5,962,705 A | 10/1999 | Didier et al. |
| 6,160,135 A | 12/2000 | Bouchard et al. |
| 6,331,635 B1 | 12/2001 | Bouchard et al. |
| 6,346,543 B1 | 2/2002 | Bissery et al. |
| 6,372,780 B2 | 4/2002 | Bouchard et al. |
| 6,387,946 B1 | 5/2002 | Bouchard et al. |
| 6,403,634 B1 | 6/2002 | Bissery |
| 7,074,821 B1 | 7/2006 | Bouchard et al. |
| 7,241,907 B2 | 7/2007 | Didier et al. |
| 7,772,274 B1 | 8/2010 | Palepu |
| 8,378,128 B2 | 2/2013 | Billot et al. |
| 8,846,959 B2 | 9/2014 | Billot et al. |
| 8,927,592 B2 | 1/2015 | Gupta |
| 2002/0038038 A1 | 3/2002 | Bouchard et al. |
| 2004/0126379 A1 | 7/2004 | Adolf et al. |

(Continued)

FOREIGN PATENT DOCUMENTS

| | | |
|---|---|---|
| CN | 1849311 A | 10/2006 |
| EP | 0817779 B1 | 1/2000 |

(Continued)

OTHER PUBLICATIONS

Winquist (The Canadian Journal of Urology, Feb. 2008, vol. 15, No. 1, pp. 3942-3949) (Year: 2008).*

(Continued)

*Primary Examiner* — James D. Anderson
(74) *Attorney, Agent, or Firm* — Kelly L. Bender

(57) ABSTRACT

The invention relates to a compound of formula:

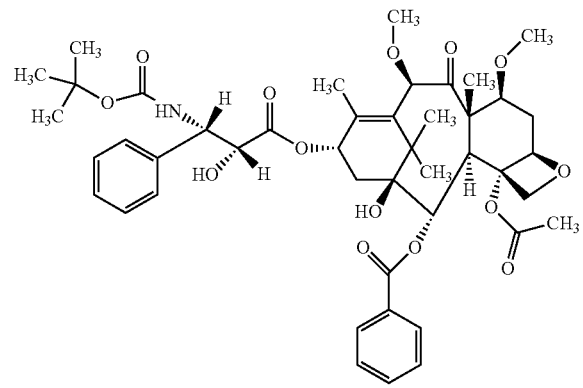

which may be in base form or in the form of a hydrate or a solvate, in combination with prednisone or prednisolone, for its use as a medicament in the treatment of prostate cancer, particularly metastatic prostate cancer, especially for patients who are not catered for by a taxane-based treatment.

6 Claims, 7 Drawing Sheets

(56) References Cited

U.S. PATENT DOCUMENTS

| | | |
|---|---|---|
| 2005/0065138 A1 | 3/2005 | Didier et al. |
| 2005/0070496 A1 | 3/2005 | Borovac et al. |
| 2005/0244413 A1 | 11/2005 | Adolf et al. |
| 2008/0076780 A1 | 3/2008 | Curwen et al. |
| 2008/0279923 A1 | 11/2008 | Bradke et al. |
| 2010/0311825 A1 | 12/2010 | Rortais et al. |
| 2011/0105598 A1 | 5/2011 | Gurjar et al. |
| 2011/0144362 A1 | 6/2011 | Billot et al. |
| 2011/0160159 A1 | 6/2011 | Ryan |
| 2011/0177970 A1 | 7/2011 | Chauchereau et al. |
| 2011/0237540 A1 | 9/2011 | Crawford et al. |
| 2012/0077845 A1 | 3/2012 | Dalton et al. |
| 2012/0115806 A1 | 5/2012 | Magherini |
| 2012/0301425 A1 | 11/2012 | Gupta |
| 2015/0118182 A1 | 4/2015 | Gupta |

FOREIGN PATENT DOCUMENTS

| | | |
|---|---|---|
| EP | 2177630 A1 | 4/2010 |
| FR | 2732340 A1 | 10/1996 |
| JP | 2007505866 A | 3/2007 |
| WO | WO-9418164 A1 | 8/1994 |
| WO | WO-9630355 A1 | 10/1996 |
| WO | WO-9630356 A1 | 10/1996 |
| WO | WO-0010547 A2 | 3/2000 |
| WO | WO-2005002846 A1 | 1/2005 |
| WO | WO-2005028462 A1 | 3/2005 |
| WO | WO-2006062811 A2 | 6/2006 |
| WO | WO-2010117668 A1 | 10/2010 |
| WO | WO-2010128258 A1 | 11/2010 |
| WO | WO-2011051894 A1 | 5/2011 |
| WO | WO-2011063421 A1 | 5/2011 |
| WO | WO-2011124669 A1 | 10/2011 |
| WO | WO-2011130317 A2 | 10/2011 |
| WO | WO-2011130566 A2 | 10/2011 |

OTHER PUBLICATIONS

Tropic Listing (http://clinicaltrials.gov/archive/NCT00417079/2006_12_28. View of NCT00417079 on Dec. 28, 2006, 3 pages) (Year: 2006).*

Mita (Clin. Cancer Res., Jan. 15, 2009, vol. 15, No. 2, pp. 723-730) (Year: 2009).*

Attard (Pathologie Biologie, 2006, vol. 54, pp. 72-84) (Year: 2006).*

Pivot (Annals of Oncology, 2008, vol. 19, pp. 1547-1552) (Year: 2008).*

Beardsley (Curr. Opin. Support Palliat. Care, 2008, vol. 2, pp. 161-166) (Year: 2008).*

Taxol (Paclitaxel) Label (Mead Johnson, Feb. 10, 2000, pp. 1-43) (Year: 2000).*

Takenaka et al. (International Journal of Urology, 2008, vol. 15, pp. 106-109) (Year: 2008).*

Hudis et al. (J. Clin. Oncol., 1996, vol. 14, pp. 58-65) (Year: 1996).*

Tannock et al. (N. Engl. J. Med., 2004, vol. 351, pp. 1502-1512) (Year: 2004).*

Declaration of Alton Oliver Sartor, M.D., as submitted in U.S. Patent and Trademark Office before the Patent Trial and Appeal Board case IPR2016-00712, U.S. Pat. No. 8,927,592, dated Jun. 23, 2016.

Curriculum Vitae for A. Oliver Sartor, M.D., dated Feb. 23, 2016.

Reply Declaration of Alton Oliver Sailor, M.D., as submitted in U.S. Patent and Trademark Office before the Patent Trial and Appeal Board case IPR2016-00712, U.S. Pat. No. 8,927,592, dated Apr. 20, 2017.

Reply Declaration of Dr. Rahul Seth, as submitted in U.S. Patent and Trademark Office before the Patent Trial and Appeal Board case IPR2016-00712, U.S. Pat. No. 8,927,592, dated Mar. 14, 2017.

Sanofi-Aventis v. Fresenius Kabi USA, Civil Action No. 14-7869, United States District Court, District of New Jersey, Sealed Opinion of Dec. 19, 2017 (redacted).

Declaration Transcript of Dr. Oliver Sartor, as submitted in U.S. Patent and Trademark Office before the Patent Trial and Appeal Board case IPR2016-00712, U.S. Pat. No. 8,927,592, dated Feb. 13, 2017.

Declaration Transcript of Dr. Oliver Sartor, as submitted in U.S. Patent and Trademark Office before the Patent Trial and Appeal Board case IPR2016-00712, U.S. Pat. No. 8,927,592, dated May 8, 2017.

Sanofi-Aventis v. Fresenius Kabi USA, Civil Action No. 14-7869, United States District Court, District of New Jersey, Excerpts from Markman Hearing held on Jan. 23, 2016, pp. 1-9, 90-105.

Sanofi-Aventis v. Fresenius Kabi USA, Civil Action No. 14-7869, United States District Court, District of New Jersey, Defendants Joint Responsive Claim Construction Brief, entered Dec. 3, 2015.

Sanofi-Aventis v. Fresenius Kabi USA, Civil Action No. 14-7869, United States District Court, District of New Jersey, Joint Claim Construction and Prehearing Statement, dated Oct. 2, 2015.

Declaration of Mr. Robert McSorley, as submitted in U.S. Patent and Trademark Office before the Patent Trial and Appeal Board case IPR2016-00712, U.S. Pat. No. 8,927,592, dated Mar. 14, 2017.

Declaration of Art Lathers, as submitted in U.S. Patent and Trademark Office before the Patent Trial and Appeal Board case IPR2016-00712, U.S. Pat. No. 8,927,592, dated Dec. 22, 2016.

Declaration Transcript of Rahul Seth, DO, as submitted in U.S. Patent and Trademark Office before the Patent Trial and Appeal Board case IPR2016-00712, U.S. Pat. No. 8,927,592, dated Dec. 9, 2016.

Declaration of Patricia Matthews, RN, BSN, as submitted in U.S. Patent and Trademark Office before the Patent Trial and Appeal Board case IPR2016-00712, U.S. Pat. No. 8,927,592, dated Jan. 16, 2017.

Sanofi-Aventis v. Fresenius Kabi USA, Civil Action No. 14-7869, United States District Court, District of New Jersey, Amended Claim Construction Opinion, Oct. 7, 2016.

Declaration Transcript of Michael Edward Tate, as submitted in U.S. Patent and Trademark Office before the Patent Trial and Appeal Board case IPR2016-00712, U.S. Pat. No. 8,927,592, dated Mar. 6, 2017.

Sanofi-Aventis v. Mylan Laboratories Limited, Civil Action No. 15-3392, United States District Court, District of New Jersey, Defendant's Answer to the Complaint, Separate Defenses and Counterclaims, 2015.

Sanofi-Aventis v. ONCO Therapies, United States District Court, District of New Jersey, Complaint for Patent Infringement, May 15, 2015.

Public Deposition of Robert McSorley, as submitted in U.S. Patent and Trademark Office before the Patent Trial and Appeal Board case IPR2016-00712, U.S. Pat. No. 8,927,592, dated Apr. 19, 2017.

Final Written Decision, as submitted in U.S. Patent and Trademark Office before the Patent Trial and Appeal Board case IPR2016-00712, U.S. Pat. No. 8,927,592, dated Sep. 21, 2017.

Aventis Pharma S.A. v. Mylan Laboratories Limited, Case No. 2018-1203, United States Court of Appeals for the Federal Circuit, Brief for Appellant, dated Mar. 15, 2018.

Patent Owner's Contingent Motion to Amend as submitted in U.S. Patent and Trademark Office before the Patent Trial and Appeal Board case IPR2016-00712, U.S. Pat. No. 8,927,592, dated Dec. 23, 2016.

Patent Owner's Response as submitted in U.S. Patent and Trademark Office before the Patent Trial and Appeal Board case IPR2016-00712, U.S. Pat. No. 8,927,592, dated Dec. 23, 2016.

Preliminary Response by Patent Owner pursuant to 37 CFR 42.107 as submitted in U.S. Patent and Trademark Office before the Patent Trial and Appeal Board case IPR2016-00712, U.S. Pat. No. 8,927,592, dated Jun. 24, 2016.

Sanofi v. Glenmark Pharmaceuticals, Civil Action No. 14-264-RGA, United States District Court, District of Delaware, Trial Opinion dated Aug. 31, 2016.

Sanofi v. Lupin Atlantic Holdings, Civil Action No. 15-415-RGA, United States District Court, District of Delaware, Trial Opinion dated Oct. 23, 2017.

Sanofi v. Watson Laboratories Inc., Case 2016-2722, U.S. Court of Appeals for the Federal Circuit, Opinion dated Nov. 9, 2017.

(56) References Cited

OTHER PUBLICATIONS

*Aventis Pharma S.A.* v. *Mylan Laboratories Limited*, Case No. 2018-1203, United States Court of Appeals for the Federal Circuit, Reply Brief for Appellant, dated May 18, 2018.
*Aventis Pharma S.A.* v. *Mylan Laboratories Limited*, Case No. 2018-1203, United States Court of Appeals for the Federal Circuit, Responsive Brief, dated Apr. 24, 2018.
A Promising R&D Portfolio, Well Positioned to Deliver Future Growth, Sanofi-Aventis Press Release, Sep. 2007, pp. 1-11.
A Randomized, Open-label, Phase 3 Study of Larotaxel IV Every 3 Weeks Versus Capecitabine (Xeloda®) Tablets Twice Daily for 2 Weeks in 3 Week Cycles in Patients with Metastatic Breast Cancer (MBC) Progressing After Taxanes and Anthracycline Therapy (EFG6089), 2012 [retrieved on Jun. 27, 2014] Retrieved from the Internet: (URL: http://en.sanofi.com/img/content/study/EFC_6089_summary.pdf).
Abrams et al., New Chemotherapeutic Agents for Breast Cancer, Cancer Suppl. 74(3), pp. 1164-1176, 1994.
Abraxane (paclitaxel) Label (May 2007).
Actavis LLC's Detailed Factual and Legal Basis for its Paragraph IV Certification that U.S. Pat. No. 8,927,592 is invalid, Unenforceable and/or Not Infringed by the [] Described in Actavis' NDA No. 207970 (2015) (redacted).
Actavis Prednisone Label (2015).
Adam's LLC'S Detailed Factual and Legal Basis for its Paragraph IV Certification that U.S. Pat. No. 8,927,592 is invalid, Unenforceable and/or Not Infringed by the [] Described in Actavis' NDA No. 207970 (2015) (redacted).
Alimta (pemetrexed) Label (Sep. 2008).
American Cancer Society Cancer Facts & Figures 2005.
American Cancer Society Cancer Facts & Figures 2009.
American Cancer Society Cancer Facts & Figures 2011.
American Cancer Society, Off-Label Drug Use, What is Off-Label Drug Use?, [retrieved from https://www.cancer.org/treatment/treatments-and-side-effects/treatment-types/chemotherapy/off-label-drug-use.html] (2017).
Andean Patent Manual. Andean Community secretary, OMPI, EPO, 2004. Section 9.4.
Anonymous, "Early study shows cabazitaxel may be more effective than docetaxel in some patients with advanced prostate cancer," American Society of Clinical Oncology, Inc., posted Apr. 3, 2015 by The ASCO Post, retrieved from internet Oct. 30, 2018 from URL http://http://www.ascopost.com/News/23626.
Antonarakis E.S., et al., "Phase III Trials with Docetaxel-Based Combinations for Metastatic Castration-Resistant Prostate Cancer," Journal of Clinical Oncology, 2013, vol. 31 (14), pp. 1709-1712.
Antonarakis et al., Novel Targeted Therapeutics for Metastatic Castration-Resistant Prostate Cancer, 291(1) Cancer Lett. 1-13 (2010), https://www.ncbi.nlm.nih.gov/pmc/articles/PMC4029098/ (published online Aug. 29, 2009).
Apotex, Detailed Statement for ANDA 207736, 2015 (redacted).
Approved Drug Products with Therapeutic Equivalence Evaluations (Orange Book), 31st Edition, 2011.
Approved Drug Products with Therapeutic Equivalence Evaluations (Orange Book), 36th Edition, 2016.
Araujo J.C., et al., "Overall Survival (OS) and Safety of Dasatinib/docetaxel Versus Docetaxel in Patients With Metastatic Castration-resistant Prostate Cancer (mCRPC): Results From the Randomized Phase III Ready Trial," Journal of Clinical Oncology, Feb. 2013, vol. 31 (6), Abstract LBA8, 3 pages as retrieved from http://ascopubs.org/doi/10.1200/jco.2013.31.6_suppl.lba8 on Oct. 30, 2018.
Archimbaud; Y., "Mouse plasma and tumor pharmacokinetics of TXD258, a new taxoid", American Association for Cancer Research, 91st Annual Meeting, Apr. 1-5, 2000, vol. 41, Abstract 1373, p. 215.
Armstrong A.J., et al., "New Drug Development in Metastatic Prostate Cancer," Urologic Oncology, 2008, vol. 26 (4), pp. 430-437.
Armstrong and Carducci, New Drugs in Prostate Cancer, 16 Curr. Opin. Urol. 138-45 (2006).

Avastin (bevacizumab), Prescribing Information (Label), Jul. 2009.
Bahl A., et al., Final quality of life and safety data for patients with metastatic castration-resistant prostate cancer treated with cabazitaxel in the UK early access programme (EAP) (NCT01254279), BJU International. vol. 116, pp. 880-887 (2015).
Bahl A., et al., 'Impact of cabazitaxel on 2-year survival and palliation of tumour-related pain in men with metastatic castration-resistant prostate cancer treated in the TROPIC trial,' Annals of Oncology, vol. 24 No. 9, pp. 2402-2408 (2013).
Baselga et al., Phase II Study of Weekly Intravenous Trastuzumab (Herceptin) in Patients with HER2/neu-Overexpressing Metastatic Breast Cancer, Semin. in Oncol. vol. 26 No. 4, Suppl. 12, pp. 78-83, 1999.
Baselga J., et al., 'Phase II study of efficacy, safety, and pharmacokinetics of trastuzumab monotherapy administered on a 3-weekly schedule,' Journal of Clinical Oncology vol. 23 No. 10, pp. 2162-2171 (2005).
Bedikian A.Y., et al., 'Phase 3 study of docosahexaenoic acid-paclitaxel versus dacarbazine in patients with metastatic malignant melanoma,' Annals of Oncology vol. 22 No. 4, pp. 787-793 (2011).
Beer et al., Phase II Study of KOS-862 in Patients with Metastatic Androgen Independent Prostate Cancer Previously Treated with Docetaxel, 25 Invest. New Drugs 565-70 (2007).
Beer T.M., et al., "Double-Blinded Randomized Study of High-Dose Calcitriol Plus Docetaxel Compared with Placebo Plus Docetaxel in Androgen-Independent Prostate Cancer: A Report from the Ascent Investigators," Journal of Clinical Oncology, 2007, vol. 25 (6), pp. 669-674.
Beeram M. et al., 'A phase I and pharmacokinetic (PK) study of the novel taxane BMS 184476 administered as a 1-hour intravenous (IV) infusion weekly,' Proceedings of ASCO vol. 20, p. 106a, Abstract 421 (2001).
Berry D.L., et al. , "Quality of Life and Pain in Advanced Stage Prostate Cancer: Results of a Southwest Oncology Group Randomized Trial Comparing Docetaxel and Estramustine to Mitoxantrone and Prednisone," Journal of Clinical Oncology, 2006, vol. 24 (18), pp. 2828-2835.
Berry W., et al., "Phase III Study of Mitoxantrone Plus Low Dose Prednisone Versus Low Dose Prednisone Alone in Patients with Asymptomatic Hormone Refractory Prostate Cancer," The Journal of Urology, 2002, vol. 168 (6), pp. 2439-2443.
Berthold D.R., et al., "Docetaxel Plus Prednisone or Mitoxantrone Plus Prednisone for Advanced Prostate Cancer: Updated Survival in the TAX 327 Study," Journal of Clinical Oncology, Jan. 10, 2008, vol. 26 (2), pp. 242-245.
Berthold Dr., et al., "Docetaxel Plus Prednisone or Mitoxantrone Plus Prednisone for Advanced Prostate Cancer: Updated Survival in the Tax 327 Study," Journal of Clinical Oncology, 2008, vol. 26 (2), pp. 242-245.
Bissery et al., Experimental Antitumor Activity of Taxotere (RP 56976, NSC 628503), a Taxol Analogue, Cancer Research 51 pp. 4845-4852, 1991.
Bissery M.C., et al., "Preclinical Evaluation of TXD258, A New Taxoid," Proceedings of the American Association for Cancer Research, 2000, vol. 41, pp. 214, Abstract No. 1364.
Booth B., et al., "Oncology's Trials," Nature Reviews, Drug Discovery, 2003, vol. 2 (8), pp. 609-610.
Bouchet B.P., et al., "Cabazitaxel, a New Taxane with Favorable Properties," Drugs of Today (Barcelona, Spain, 2010, vol. 46 (10), pp. 735-742.
BPI's Detailed Factual and Legal Bases in Support of its Paragraph IV Certification for Cabazitaxel Solution. IV, 2015 (redacted).
Brady, Urological Institute Johns Hopkins Medical Institutions, New Drugs for Prostate Cancer: Chemotherapy Transformed, vol. VI, 1-2, 2003.
Bristol-Myers Squibb, 'In the pipeline Dec. 31, 2014,' URL: http://www.bms.com/research/pipleline/Pages/default.aspx. Retrieved on Aug. 5, 2016.
Bristol-Myers Squibb Reports Results for Phase 3 Trial of Yervoy (Ipilimumab) in Previously•Treated Castration Resistant Prostate Cancer, Press Release Sep. 12, 2013 [retrieved on Jun. 27, 2014] Retrieved from the Internet: (URL:http://news.bms.com/press-release/rd-news/bristol-myers-squibb-reports-results-phase-3-trial-yervoy-ipilimumab-previous).

(56) References Cited

OTHER PUBLICATIONS

Brooks, FDA Grants Expanded Indication for Enzalutamide (Xtandi) MEDSCAPE, 2004 (http://www.medscape.com/viewarticle/831548) (retrieved on Mar. 13, 2017).
Buonerba C., et al., "Docetaxel Rechallenge in Castration-Resistant Prostate Cancer: Scientific Legitimacy of Common Clinical Practice," European Urology, 2010, vol. 58 (4), pp. 636-637.
Butler M.S., et al., "Natural Products to Drugs: Natural Product-Derived Compounds in Clinical Trials," Natural Product Reports, 2008, vol. 25 (3), pp. 475-516.
Byrn, S.R., et al., 'Solid-state chemistry of drugs,' 2nd edition, SSCI, Inc., pp. 12-13, 233 and 516-517 (1999).
Cabazitaxel (XRP-6258) for hormone refractory, metastatic prostate cancer second line after docetaxel, National Horizon Scanning Centre, National Institute for Health Research, University of Birmingham, Apr. 2009, pp. 1-5.
Cabral F., et al., "Factors Determining Cellular Mechanisms of Resistance to Antimitotic Drugs," Drug Resistance Updates, 2001, vol. 4 (1), pp. 3-8.
Cabrespine, et al., Randomized Phase II Study Comparing Paclitaxel and Carboplatin Versus Mitoxantrone in Patients with Hormone-Refractory Prostate Cancer, Urology, 67(2), 354-359 (2006).
Caffo et al., Pemetrexed as Second-Line Chemotherapy for Castration-Resistant Prostate Cancer After Docetaxel Failure: Results from a Phase II Study, 31(2) Urol. Oncol. 180-86 (2013).
Camptosar (irinotecan) Label (Jul. 2005).
Cancer de Prostata Diseminado, Quimioterapia, [Retrieved on Jul. 29, 2014] pp. 1-9. Retrieved from the internet: (URL:http://www.guiasalud.es/egpc/cancer_Prostata/resumida/apartado06/otros02.html).
Cancer Therapy Evaluation Program Common Toxicity Criteria, Version 2.0, DCTD, NCI; NIH, DHHS. revised Mar. 1998, published Apr. 30, 1999, pp. 1-35.
Canil C.M., et al., "Is There a Role for Chemotherapy in Prostate Cancer?," British Journal of Cancer, 2004, vol. 91, pp. 1005-1011.
Canil et al., Randomized Phase II Study of Two Doses of Gefitinib in Hormone-Refractory Prostate Cancer: A Trial of the National Cancer Institute of Canada-Clinical Trials Group, 23(3) J. Clin. Oncol. 455-60 (2005).
Carducci M.A., 'Atrasentan, an endothelin-receptor antagonist for refractory adenocarcinomas: safety and pharmacokinetics,' Journal of Clinical Oncology vol. 20 No. 8, pp. 2171-2180 (2002).
Carducci M.A., et al., "A Phase 3 Randomized Controlled Trial of the Efficacy and Safety of Atrasentan in Men with Metastatic Hormone-Refractory Prostate Cancer," Cancer, 2007, vol. 110 (9), pp. 1959-1966.
Carlson et al., Breast Cancer-Clinical Practice Guidelines in Oncology, 7(2) J. National Comprehensive Cancer Network 122-92 (2009).
Carlson R.O., et al., "New Tubulin Targeting Agents Currently in Clinical Development," Expert Opinion on Investigational Drugs, 2008, vol. 17 (5), pp. 707-722.
CBO Promotional Spending for Prescription Drugs, pp. 1-8, Dec. 2, 2009.
Chemotherapy for Prostate Cancer, American Cancer Society, Retrieved from the internet on Oct. 6, 2016 at https://www.cancer.org/cancer/prostate-cancer/treating/chemotherapy.html.
Chen et al., Gefitinib Treatment is Highly Effective in Non-Small-Cell Lung Cancer Patients Failing Previous Chemotherapy in Taiwan: A Prospective Phase II Study, J. Chemother. 17(6) pp. 679-684, 2005.
Chen, Optimal Adaptive Group Sequential Design for Phase II Clinical Trials A Bayesian Decision Theoretic Approach. ProQuest LLC, 2008, 134 pages.
Cisternino S., et al., "Nonlinear Accumulation in the Brain of the New Taxoid Txd258 Following Saturation of P-Glycoprotein at the Blood-Brain Barrier in Mice and Rats," British Journal of Pharmacology, 2003, vol. 138 (7), pp. 1367-1375.
ClinicalTrials.gov, A Study to Evaluate the Effects of Combining Cabazitaxel with Cisplatin Given Every 3 Weeks in Patients With Advanced Solid Cancer, Jul. 22, 2009, pp. 1-7 [retrieved on Jan. 6, 2014 from https://clinicaltrials.gov/ct2/show/NCT00925743?cond=NCT00925743&rank=1].
ClinicalTrials.gov, BMS-184476 in treating patients with advanced solid tumors, p. 1, retrieved on Aug. 5, 2015 from https://clinicaltrials.gov/ct2/results?term=BMS-184476&Search=Search.
ClinicalTrials.gov, 'BMS-188797,' p. 1, retrieved on Aug. 5, 2015 from https://clinicaltrials.gov/ct2/results?term=BMS-188797&Search=Search.
ClinicalTrials.gov, 'BMS-275183,' p. 1, retrieved on Aug. 5, 2015 from https://clinicaltrials.gov/ct2/results?term=BMS-275183&Search=Search.
ClinicalTrials.gov, Effect of Cabazitaxel on the QTc Interval in Cancer Patients (QT-Cab), Web site, Mar. 24, 2010, pp. 1-7 [retrieved on Jan. 6, 2014].
ClinicalTrials.gov, Efficacy and Safety of BG00012 in MS (Sep. 14, 2005), https://clinicaltrials.gov/archive/NCT00168701/2005_09_14, pp. 1-6.
ClinicalTrials.gov, Larotaxel every 3 weeks vs. capecitabine patients with metastatic breast cancer progressing after taxanes and anthracycline therapy [retrieved on Jun. 24, 2014] Retrieved from the Internet (URL: https://clinicaltrials.gov/ct2/show/NCT000081796?term==larotaxel&rank=7).
ClinicalTrials.gov, Larotaxel plus cisplatin vs gemcitabine plus cisplatin in first line treatment of patients wtth locally advanced/metastatic bladder cancer [retrieved on Jun. 24, 2014]. Retrieved from the Internet (URL: https://clinicaltrials.gov/ct2/show/NCT00625664?term=larotaxel&rank=4).
ClinicalTrials.gov, Larotaxel vs. 5-FU or capecitabine in patients with pancreatic cancer previously treated with gemcitabine [retrieved Jun. 24, 2014] Retrieved from the Internet (URL: https://clinicaltrials.gov/c2/show/NCT00417209?Term=larotaxel&rank=2).
ClinicalTrials.gov, MST-997, p. 1, retrieved on Aug. 5, 2015 from https://clinicaltrials.gov/ct2/results?term=MST-997&Search=Search.
ClinicalTrials.gov, Patient Preference Between Cabazitaxel and Docetaxel in Metastatic Castrate-Resistant Prostate Cancer (CABA-DOC), Retrieved from the internet on Dec. 21, 2016 at https://clinicaltrials.gov/ct2/show/study/NCT02044354.
ClinicalTrials.gov, Protocol Registration Preview, A study to evaluate the effects of combining cabazitaxel with cisplatin given every 3 weeks in patients with advanced solid cancer, Website, pp. 1-3, retrieved on Nov. 12, 2009.
ClinicalTrials.gov, Safety and Pharmacokinetic Study of Cabazitaxel in Patients With Advanced Solid Tumors and Liver Impairment Web site, 2010, pp. 1-7 [retrieved on Jan. 6, 2014].
ClinicalTrials.gov, Satraplatin in Hormone Refractory Prostate Cancer Patients Previously Treated with one Cytotoxic Chemotherapy Regimen [retrieved on Jun. 27, 2014]. Retrieved from the Internet:( URL: https//clinicaltrials.gov/ct2/show/NCT00069745?term=SPARC&cond=prostate&rank=3).
ClinicalTrials.gov, Tesetaxel, p. 1-2, retrieved on Aug. 5, 2015 from https://clinicaltrials.gov/ct2/results?term=tesetaxel&Search=Search.
ClinicalTrials.gov, TL-310, p. 1, retrieved on Aug. 5, 2015 on https://clinicaltrials.gov/ct2/results?term=TL-310&Search=Search.
ClinicalTrials.gov, TPI-287, p. 1-2, as retrieved on Aug. 5, 2015 from https://clinicaltrials.gov/ct2/results?term=TPI-287&Search=Search.
ClinicalTrials.gov, XRP6258 Plus Prednisone Compared to Mitoxantrone Plus Prednisone in Hormone Refractory Metastatic Prostate Cancer (TROPIC), Archived Oct. 23, 2008, (https://web.archive.org/web/20081023121613/http://clinicaltrials.gov/ct2/show/NCT00417079) (last accessed: Mar. 14, 2017).
Cobleigh et al., Multinational Study of the Efficacy and Safety of Humanized Anti-HER2 Monoclonal Antibody in Women who have HER2-Overexpressing Metastatic Breast Cancer that has Progressed After Chemotherapy for Metastatic Disease, J. Clin. Oncol. 17(9), pp. 2639-2648, 1999.
Collins R., et al., "A Systematic Review and Economic Model of the Clinical Effectiveness and Cost-Effectiveness of Docetaxel in Combination With Prednisone or Prednisolone for the Treatment of

(56) References Cited

OTHER PUBLICATIONS

Hormone-Refractory Metastatic Prostate Cancer," Health Technology Assessment, 2007, 11 (2), pp. 1-179.
U.S. Appl. No. 61/256,160, filed Oct. 29, 2009.
U.S. Appl. No. 61/293,903, filed Jan. 11, 2010.
U.S. Appl. No. 61/355,834, filed Jun. 17, 2010.
Dagher et al., Approval Summary: Docetaxel in Combination with Prednisone for the Treatment of Androgen-Independent Hormone-Refractory Prostate Cancer, Clinical Cancer Research 8147-51 (2004).
Dagher R., et al., "Approval Summary: Docetaxel in Combination with Prednisone for the Treatment of Androgen-Independent Hormone-Refractory Prostate Cancer," Clinical Cancer Research, 2004, vol. 10 (24), pp. 8147-8151.
D'Amico A.V., et al., "US Food and Drug Administration Approval of Drugs for the Treatment of Prostate Cancer: A New Era has Begun," Journal of Clinical Oncology, 2014, vol. 32 (4), pp. 362-364.
Daniel Zuccerinho, Patents of Invention, Ed. Abele do Perrot, 1999.
De Bono, et al., Cabazitaxel or Mitoxantrone With Prednisone in Patients With Metastatic Castration-Resistant Prostate Cancer (mCRPC) Previously Treated With Docetaxel: Final Results of a Multinational Phase III Trial (TROPIC), 46th Annual Meet American Society Clinical Oncology (ASCO), Journal of Clinical Oncology, 2010, 28:15S (Suppl), Abstract 4508.
De Bono et al., Phase III non-inferiority study of cabazitaxel (C) 20 mg/m2 (C20) versus 25 mg/m2 (C25) in patients (pts) with metastatic castration-resistant prostate cancer (mCRPC) previously treated with docetaxel (D), ASCO Annual Meeting 2016, pp. 1-2, 2016.
De Bono, et al., Prednisone Plus Cabazitaxel or Mitoxantrone for Metastatic Castration-Resistant Prostate Cancer Progressing after Docetaxel Treatment a Randomised Open-Label Trial, Lancet, 2010, vol. 376, No. 9747, pp. 1147-1154.
De Bono J.S., et al., "Cabazitaxel or Mitoxantrone with Prednisone in Patients with Metastatic Castration-Resistant Prostate Cancer (mCRPC) Previously Treated with Docetaxel Final Results of a Multinational Phase III Trial (TROPIC)," Journal of Clinical Oncology, 2010, vol. 28, pp. 155.
De Bono J.S., et al., 'Open-label phase II study evaluating the efficacy and safety of two doses of pertuzumab in castrate chemotherapy-naïve patients with hormone-refractory prostate cancer,' Journal of Clinical Oncology, vol. 25 No. 3, pp. 257-262 (2007).
Deakin and Williams, Histamine H2-Receptor Antagonists in Peptic Ulcer Disease, Efficacy in Healing Peptic Ulcers, 44(5) Drugs 709-19 (1992).
Denis L.J, et al., "Phase I and Pharmacokinetic Study of RPR116258A. A Novel Taxane Derivative, Administered Intravenously over 1 hour every 3 weeks," Clinical Cancer Research, 2000, vol. 6, pp. 4579s, Abstract 568.
Detailed Factual and Legal Bases for Breckenridge's Paragraph IV Certification that U.S. Pat. No. 8,927,592 Is Invalid, Unenforceable and/or Will Not Be infringed, 2015 (redacted).
Detailed Statement of the Factual and Legal Bases for Onco Therapies Limited's Paragraph IV Certification with Respect to U.S. Pat. No. 8,927,592, 2015 (redacted).
Dieras et al., Larotaxel in Combination with Trastuzumab in Patients with HER2+ Metastatic Breast Cancer: Interim Analysis of an Open Phase II Label Study, 26 (15S), J. Clin. Oncol. (Meeting Abstracts), Suppl. 1070, May 2008.
Dieras V., et al., "Phase II Multicenter Study of Larotaxel (Xrp9881), a Novel Taxoid, in Patients with Metastatic Breast Cancer Who Previously Received Taxane-Based Therapy," Annals of Oncology, 2006, vol. 19 (7), pp. 1255-1260.
Dilorenzo G., et al., "Castration-Resistant Prostate Cancer: Current and Emerging Treatment Strategies," Drugs, 2010, vol. 70 (8), pp. 983-1000.
Dilorenzo G., et al., "Combination of Bevacizumab and Docetaxel in Docetaxel-Pretreated Hormone-Refractory Prostate Cancer: A Phase 2 Study," European Urology, 2008, vol. 54 (5), pp. 1089-1096.

Dimasi J.A., et al., "Economics of New Oncology Drug Development," Journal of Clinical Oncology, 2007, vol. 25 (2), pp. 209-216.
Dimasi J.A., et al., "Trends in Risks Associated with New Drug Development Success Rates for Investigational Drugs," Clinical Pharmacology and Therapeutics, 2010, vol. 87 (3), pp. 272-277.
Docetaxel Label (Mar. 2012).
Docetaxel Reduce el Riesgo de Muerte en Pacientes con cancer de Prostata metastatico Androgeno Independiente, [Retrieved on Jul. 29, 2014]. Retrieved from the internet: (URL: http://www.intramed.net/contenidover.asp?contenidoID=31823) (followed by non-verified English translation).
Docetaxel (Taxotere) y Cancer de Próstata. Retrieved from the internet: (URL: http.//www.newsmedical.net/health/docetaxel-(taxotere)-and-prostate-cancer-(spanish).aspx).
Doenicke, et al., Premedication with H1 and H2 blocking agents reduces the incidence of postoperative nausea and vomiting, Inflam. Res., 53, Suppl. 2, 51-58, (2004).
Dorff T.B., et al., "Cabazitaxel in Prostate Cancer: Stretching a String," Lancet, 2010, vol. 376 (9747), pp. 1119-1120.
Dres, et al., Treatment alternatives for advanced prostate cancer, [Retrieved from the internet on Jul. 29, 2014] Retrieved from http://www.intramed.net/contenidoverasp?conteniID=37957 (followed by non-verified English translation), 3 pages.
Drug Data Report, Antimitotic Drugs, 2003, vol. 25, No. 6, pp. 550.
Drug Data Report Cabazitaxel, 2010, vol. 32, No. 10, pp. 999-1017 at p. 1012.
Dumontet C., et al., "Mechanisms of Action of and Resistance to Antitubulin Agents: Microtubule Dynamics, Drug Transport, and Cell Death," Journal of Clinical Oncology, 1999, vol. 17 (3), pp. 1061-1070.
Eisenberger, M., et al., Phase III Study comparing a reduced dose of cabazitaxel (20 mg/m2) and the currently approved dose (25 mg/m2) in postdocetaxel patients with metastatic castration-resistant prostate cancer—PROSELICA, J. Clin. Oncol., vol. 35, as downloaded from http://ascopubs.org/journal/jcoon Sep. 22, 2017, 13 pages.
Eisenhauer E.A., et al., "Phase I Cancer Clinical Trials: A Practical Guide," Basics of Phase I Design: First-in-Man Studies, Oxford University Press, 2006, pp. 42-80.
El Docetaxel Asociado a la Prodnisona Mejora el Cancer de Prostata, [Retrieved from the internet on Oct. 26, 2012] Retrieved from internet:(URL: http://www.medicinageriatrica.com.ar/viewnews.php?id=E.EpVVFZVppsBCjOavj).
El-Maraghi and Eisenhauer, Review of Phase II Trial Designs Used in Studies of Molecular Targeted Agents: Outcomes and Predictors of Success in Phase III, J. Clin. Oncol. 26 (2008) 1346-1354.
Emcyt (estramustine) Label (Jun. 2007).
Engels, F.K., et al., 'Potential for improvement of docetaxel-based chemotherapy: a pharmacological review,' British Journal of Cancer, vol. 93, pp. 173-177 (2005).
Erbitux (cetuximab) Label (Jul. 2009).
Esper and Redman, Supportive Care, Pain Management, and Quality of Life in Advanced Prostate Cancer, 26(2) Urologic Clinics of North America 375-89 (1999).
Estramustine, Chemocare.com, retrieved from the internet at http://chemocare.com/chemotherapy/drug-info/estramustine.aspx on Mar. 8, 2017.
European Medicine Agency, ICH Topic E8 General Considerations for Clinical Trials (Mar. 1998).
Factual and Legal Bases for Accord's ANDA Certification That Each Claim of U.S. Pat. No. 8,927,592 is Invalid, Unenforceable, and/or Will Not Be Infringed by Accord's Cabazitaxel Injection Product Described in ANDA 207693 (2015) (redacted).
Factual and Legal Basis for Dr. Reddy's Laboratories, Ltd.'s and Dr. Reddy's Laboratories, Inc.'s Assertion of Invalidity, Unenforceability and/or Non-Infringement of U.S. Pat. No. 8,927,592, 2015 (redacted).
FDA Approves New Drug for Advanced Prostate Cancer (May 15, 2013), retrieved from http://www.fda.gov/NewsEvents/Newsroom/PressAnnouncements/ucm352363.htm, retrieved on Oct. 6, 2016.
FDA Center for Drug Evaluation and Research, Clinical Pharmacology and Biopharmaceutics Review(s), Application No. 201023 (Cabazitaxel NDA), 2010, pp. 1-71.

(56) References Cited

OTHER PUBLICATIONS

FDA, Challenge and Opportunity on the Critical Path to New Medical Products, 1-31 (Mar. 2004).
FDA News Release, FDA Approves New Indication for Taxotere—Prostate Cancer (May 19, 2004) as retrieved from http://www.fda.gov/NewsEvents/Newsroom/PressAnnouncements/2004/ucm108301.htm.
FDA News release, FDA Approves New Treatment for Advanced Prostate Cancer, 2010, pp. 1-2, [Retrieved on Jul. 29, 2015]. Retrieved from the internet (URL: http://www.fda.gov.newsevents/newsroom/pressannouncements/ucm216143.htm].
FDA Notice International Conference on Harmonisation; Guidance on Impurities: Residual Solvents, 62(247) Federal Register 67377-388 (Dec. 24, 1997).
Feuerstein A., et al., 'Oncology Micro-Cap Stocks: Caveat Emptor!' Journal of the National Cancer Institute, vol. 103, issue 20 pp. 1488-1489 (2011).
Figg W.D., et al., "Cabazitaxel: Filling One of the Gaps in the Treatment of Prostate Cancer," Cancer Biology & Therapy, 2010, vol. 10 (12), pp. 1233-1234.
Final Office Action dated Sep. 16, 2013 for U.S Appl. No. 13/456,720, filed Apr. 26, 2012.
Fizaz K., et al., "New agents in Metastatic Prostate Cancer," European Journal of Cancer, 2009, vol. 45 (1), pp. 379-380.
Fizazi K., 'Phase III, randomized, placebo-controlled study of docetaxel in combination with zibotentan in patients with metastatic castration-resistant prostate cancer,' Journal of Clinical Oncology vol. 31 No. 14, pp. 1740-1747 (2013).
Fresenius Kabi USA, LLC's Detailed Statement of the Factual and Legal Bases of Fresenius Kabi USA, LLC's Opinion that U.S. Pat. No. 8,927,592 Is Invalid, Unenforceable or Not infringed, 2015 (redacted).
Fujisaka et al., Phase 1 Study of Atrasentan (ABT627), Novel Endothelin Receptor-A Antagonist, in Japanese Patients with Hormone Refractory Prostate Cancer, 24(18S) J. Clin. Oncol. (Abstr. 14602) (2006).
Fukuoka M., 'Multi-institutional randomized phase II trial of Gefitinib for previously treated patients with advanced non-small-cell lung cancer,' Journal of clinical oncology, vol. 21, No. 12, pp. 2237-2246 (2003).
Fumoleau et al., Phase I and Pharmacokinetics (PK) Study of RPR116258A Given as a Weekly 1-Hour Infusion at Day 1, Day 8, Day 15, Day 22 Every 5 Weeks in Patients (pts) with Advanced Solid Tumors, 7(11) Clin. Cancer Res. 3710s (2001).
Gad, Clinical Trials Handbook (John Wiley & Sons. Inc.), 2009 Regulatory Requirements for Investigational New Drug, pp. 23-69.
Gallagher M.L., et al., 'Phase I clinical and pharcokinetic (PK) trial of the novel taxane BMS-184476 administered as a 1-hour IV infusion in combination with cisplatin every 21 days,' Proceedings of ASCO vol. 20, Abstract 420, (2001).
Galletti E., et al., "Paclitaxel and Docetaxel Resistance: Molecular Mechanisms and Development of New Generation Taxanes," Chemmedchem, 2007, vol. 2 (7), pp. 920-942.
Galsky M.D., et al., "Cabazitaxel," Nature Reviews, Drug Discovery, 2010, vol. 9 (9), pp. 677-678.
Garcia et al., Gemcitabine and Docetaxel in Metastatic, Castrate-Resistant Prostate Cancer, 117(4) Cancer 752-57 (2011).
Gayther, et al., The Frequency of Germ-line Mutations in the Breast Cancer Predisposition Genes BRCA1 and BRCA2 in Familial Protate Cancer, Cancer Res. 60 (2000) 4513-4518.
Gemzar (gemcitabine) Label Apr. 2006.
Genentech Provides Update on Phase III Study of Avastin in Men with Late Stage Prostate Cancer (Mar. 12, 2010), Business Wire, as retrieved from http://www.businesswire.com/news/home/20100311007023/en/Genentech-Update-Phase-III-Study-Avastin-Men on Oct. 12, 2016.
Gianni et al., Nonlinear Pharmacokinetics and Metabolism of Paclitaxel and Its Pharmacokinetic/Pharmacodynamic Relationships in Humans, 13(1) J. Clin. Oncol. 180-90 (1995).
Gleevec (imatinib) Label (May 2009).

Glenmark's Detailed Statement of the Factual and Legal Basis for its Opinion that U.S. Pat. No. 8,927,592 is invalid, unenforceable and/or will not be infringed by Glenmark's manufacture, use, offer for sale or sale of Glenmark's [], 2015 (redacted).
Goetz et al., "Phase I: and Pharmacokinetic Study of RPR116258A, a Novel Taxane Derivative, Administered Intravenously Over 1 Hour Every 3 Weeks," Clinical Pharmacology, 2001, vol. 20, pp. 106a.
Goffin J., et al., 'Objective responses in patients with malignant melanoma or renal cell cancer in early clinical studies do not predict regulatory approval,' Clin. Cancer Res. 11, pp. 5928-5934 (2005).
Greene et al., Who is the Average Patient Presenting with Prostate Cancer?, 66(5 Suppl.) Urology 76-82 (2005).
Guidance for Industry Population Pharmacokinetics, U.S. Department of Health and Human Services, Food and Drug Administration, CDER, CBER, Feb. 1999, 35 Pages.
Gujarat Cancer & Research Institute Annual Report, Aug. 29, 2008, pp. 1-152.
Hait W.N., et al., "Rational Design and Pre-clinical Pharmacology of Drugs for Reversing Multidrug Resistance," Biochemical Pharmacology, Jan. 1992, vol. 43 (1), pp. 103-107.
Halabi S., et al., "Prostate-Specific Antigen Changes as Surrogate for Overall Survival in Men with Metastatic Castration-Resistant Prostate Cancer Treated with Second-Line Chemotherapy," Journal of Clinical Oncology, 2013, vol. 31 (31), pp. 3944-3950.
Haleblian, "Characterization of Habits and Crystalline Modification of Solids and Their Pharmaceutical Applications," Journal of Pharmaceutical Sciences, 1975, vol. 64 (8), pp. 1269-1288.
Hande, The Importance of Drug Scheduling in Cancer Chemotherapy: Etoposide as an Example, 1(4) The Oncologist 234-29 (1996).
Hellerstedt B.A., et al., "The Current State of Hormonal Therapy for Prostate Cancer," CA a Cancer Journal for Clinicians, 2002, vol. 52 (3), pp. 154-179.
Herceptin (trastuzumab) Label Jan. 2008.
Higano C.S., et al., "Phase 1/2 Dose-Escalation Study of a Gm-Csf-Secreting, Allogeneic, Cellular Immunotherapy for Metastatic Hormone-Refractory Prostate Cancer," Cancer, 2008, vol. 113 (5), pp. 975-984.
Holen et al., Phase I Study Using Continuous Intravenous (CI) KOS-862 (Epothilone D) in Patients with Solid Tumors, 22(14S) J. Clin. Oncol. Abstr. 2024 (2004).
Hope, J., 'Last Hope' drug for Prostate Cancer Patients is axed from the NHS, DailyMail.com, Retrieved from http://www.dailymail.co.uk/health/article-2903235/Last-hope-drug-prostate-cancer-patients-axed-NHS-doctors-call-travesty.html on Oct. 20, 2016.
Horwitz E.M., et al., "External Beam Radiation Therapy for Prostate Cancer," CA a Cancer Journal for Clinicians, 2000, vol. 50 (6), pp. 349-379.
Hospers, et al., PET Imaging of Steroid Receptor Expression in Breast and Prostate Cancer, Curr. Pharm. Des. 14 (2008) 3020-3032.
How XTANDI works, as retrieved from https://www.xtandi.com/how-xtandi-works on Oct. 6, 2016, pp. 1-2.
How ZYTIGA (abiraterone acetate) works, https://www.zytiga.com/about-zytiga/how-zytiga-works, pp. 1-6 as retrieved on Nov. 16, 2016.
How ZYTIGA (abiraterone acetate) Works, Retrieved from the internet on Nov. 16, 2016 at https://www.zytigo.com/about-zytiga/how-zytiga-works.
Hycamtin (topotecan) Label Jun. 2006.
In a Difficult Environment, Another Year of Growth in Adjusted EPS Excluding Selected Items, Sanofi-Aventis Press Release, 2006 (Feb. 13, 2007), pp. 1-31.
In the United States District Court for the District of New Jersey, Case 3:15-cv-03392-MAS-LHG, Defendant's Answer to the Complaint, Separate Defenses and Counterclaims, *Mylan Laboratories Limited* v. *Aventis Pharma S.A*, 20 pages, dated Jul. 16, 2015.
Institut National du Cancer, Register of French cancer clinical trials, Sanofi-Aventis TROPIC, Feb. 29, 2008, ("INDC website"), pp. 1-2.
International Preliminary Report on Patentability for Application No. PCT/IB2010/054866, dated Nov. 14, 2011, 14 pages.
International Search Report and Written Opinion issued in WO2011/051894 dated May 5, 2011, 11 pages.

(56) References Cited

OTHER PUBLICATIONS

Iressa (gefitinib) Label (Jul. 2004).
IXEMPRA Prescribing Information (Labelling), 2007, pp. 1-34.
Jevtana (cabazitaxel) Label (Sep. 2016).
Jevtana (cabazitaxel) Label (Jun. 2015).
Jevtana label 2010—Prescribing Information, pp. 1-25, (retrieved on May 14, 2013). Retrieved from the Internet:( URL: http/products.sanofi.us/jevtana/jevtana.html).
Jevtana National Drug Monograph, pp. 1-14, 2011.
Jevtana NDA Clinical Overview, Excerpt, 2014, pp. 12-13.
Joffe et al., Quality of Informed Consent in Cancer Clinical Trials: A Cross-Sectional Survey, 358 The Lancet 1772-77 (2001).
Jozwiakowski, Alteration of the Solid State of the Drug Substance: Polymorphs, Solvates, and Amorphous Forms, Ch. 15, Water Insoluble Drug Formulation edited by Liu, First Edition, (2000) 525-568.
Kant J., et al., "A Chemoselective Approach to Functionalize the C-10 Position of 10-Deacetylbaccatin III Synthesis and Biological Properties of Novel C-10 Taxol® Analogues," Tetrahedron Letters, 1994, vol. 35 (31), pp. 5543-5546.
Kaur M., et al., "Suramin's Development: What Did We Learn?," Investigational New Drugs, 2002, vol. 20 (2), pp. 209-219.
Kawaguchi, et al., H2 Blockers Increase Risk of Docetaxel-Induced Skin Toxicity, Reactions 1257 (Jun. 20, 2009).
Kelland et al., Comparative in vitro cytotoxicity of taxol and Taxotere against cisplatin-sensitive and -resistant human ovarian carcinoma cell lines, Cancer Chemother. Pharmacol. (1992) 444-450.
Ketoconazole in Advanced Prostate Cancer: Have Tolerability Concerns Been Overstated? Drug Ther. Perspect. 15 (2000) (http://www.medscape.com/viewarticle/406391) (last accessed: Mar. 14, 2017).
Kingston D.G., et al., "Tubulin-Interactive Natural Products as Anticancer Agents," Journal of Natural Products, 2009, vol. 72 (3), pp. 507-515.
Kish J.A., et al., "The Treatment Challenge of Hormone-refractory Prostate Cancer," Cancer Control, Nov.-Dec. 2001, vol. 8 (6), pp. 487-495.
Klein et al., SWOG-9510: Evaluation of Topotecan in Hormone Refractory Prostate Cancer: A Southwest Oncology Group Study, 52(4) The Prostate 264-68 (2002).
Kobayashi K., et al., "Phase I Study of Suramin Given by Intermittent Infusion Without Adaptive Control in Patients With Advanced Cancer," Journal of Clinical Oncology, Sep. 1995, vol. 13 (9), pp. 2196-2207.
Kola I., et al., "Can the Pharmaceutical Industry Reduce Attrition Rates?," Nature Reviews, Drug Discovery, 2004, vol. 3 (8), pp. 711-715.
Koletsky A.,et al., "Developing Treatments for Hormone-Refractory Prostate Cancer," US Oncology Review, 2008, vol. 4(1), pp. 46-49.
Kris M.G., et al., "Clinical Cancer Advances 2010: Annual Report on Progress Against Cancer from the American Society of Clinical Oncology," Journal of Clinical Oncology, 2010, vol. 28 (36), pp. 5327-5347, 947.
Latif et al., Phase II Study of Oral Bis(Aceto) Ammine Dichloro (Cyclohexamine) Platinum (IV) (JM-216, BMS-1892751) Given Daily x5 in Hormone Refractory Prostate Cancer (HRPC), Investig. New Drugs 79-84 (2005).
Lin et al., A Phase II Trial of Imatinib Mesylate in Patients with Biochemical Relapse of Prostate Cancer After Definitive Local Therapy, 98 BJU Int'l. 763-69 (2006).
Lokich and Anderson, Dose Intensity for Bolus Versus Infusion Chemotherapy Administration: Review of the Literature for 27 Anti-Neoplastic Agents, 8(1) Ann. Oncol. 15-25 (1997).
Lortholary et al., "Phase I and Pharmacokinetics (PK) Study of RPR 116258A Given as 1-hour Infusion inPatients (pts) with Advanced Solid Tumors," Clinical Cancer Research, 2000, vol. 6, pp. 4579s-4580s.
Ma, et al., A Statistical Analysis of the Magnitude and Composition of Drug Promotion in the United States in 1998, Clin. Therap. 25 (2003) 1503-1517.

MacKinnon A.C., et al., "Molecular Biology Underlying the Clinical Heterogeneity of Prostate Cancer: An Update," Archives of Pathology & Laboratory Medicine, 2009, vol. 133 (7), pp. 1033-1040.
Malhotra et al., Cabazitaxel: A Novel Drug for Hormone-Refractory Prostate Cancer, Mini-Reviews in Medicinal Chemistry, 2013, 13, No. 2, pp. 1-6.
Malik Z., et al., '931P—Cabazitaxel (CBZ) + prednisone (P: CBZP) in patients (pts) with metastatic castration-resistant prostate cancer (mCRPC) previously treated with doce . . . ' Poster presented at ESMO Congress 2012.
Malik Z.I., et al., 'Cabazitaxel (Cbz) + prednisone (P) in patients (pts) with metastatic castration-resistant prostate cancer (mCRPC) previously treated with docetaxel (D): interim results from compassionate-use programme (CUP) and early-access programme (EAP),' Poster 931P presented at European Society for Medical Oncology, Vienna Austria, Sep. 28-Oct. 2, 2012.
Malik Z.I., et al., 'Cabazitaxel (CBZ) + Prednisone (P; CBZP) in Patients (PTS) With Metastatic Castration-Resistant Prostate Cancer (MCRPC) Previously Treated With Docetaxel (D): Interim Results From Compassionate-Use Programme (CUP) and Early-Access Programme (EAP),' Poster 931P, Annals of Oncology vol. 23, Suppl. 9 Abstract Book of the ESMO 2012 Congress, pp. 1-6 (2012).
Manchanda, et al., The Effects and Role of Direct-to-Physician Marketing in the Pharmaceutical Industry: An Integrative Review, Yale J. Health Pol'y L. & Ethics 5 (2005) 785-822.
Manual of Patent Examining Procedure §2107.03 (IV), 2008, 2100-36 (8th Ed).
McKeage et al., A Phase I and Pharmacology Study of an Oral Platinum Complex, JM216: Dose-Dependent Pharmacokinetics with Single-Dose Administration, Cancer Chemother. Pharmacol. 451-8 (1995).
McLeod H.L., et al., "Evaluation of the Linearity of Docetaxel Pharmacokinetics," Cancer Chemotherapy and Pharmacology, Jun. 1998, vol. 42 (2), pp. 155-159.
Melzack R., et al., "The McGill Pain Questionnaire: Major Properties and Scoring Methods," Pain, 1975, vol. 1(3), pp. 277-299.
Merck Index 14th 2006, No. 190, pp. 35, Agomelatine.
Michael, et al., Prostate Cancer Chemotherapy in the Era of Targeted Therapy, Prostate Cancer Prostatic Dis. 13-16 (2009).
Michaelson M.D., et al. , "Randomized, Placebo-Controlled. Phase III Trial of Sunitinib Plus Prednisone Versus Prednisone Alone in Progressive, Metastatic, Castration-Resistant Prostate Cancer," Journal of Clinical Oncology, 2014, vol. 32 (2), pp. 76-82.
Mirtsching, Prostate Cancer Clinical Trials in Dallas, Texas Area, [Retrieved from the internet on Aug. 19, 2014], pp. 3-4, Retrieved from the internet: (URL: http://www.heallhcentral.com/prostate/c/5618/14589/dallas-texas-area).
Mitoxantrone, Chemocare.com, retrieved from the internet at http://chemocare.com/chemotherapy/drug-info/Mitoxantrone.aspx on Mar. 8, 2017.
Miura N., et al., "A Case of Hormone-Refractory Prostate Cancer (Hrpc) with Tumor Fever Responding to Docetaxel Plus Prednisolone Therapy," Jpn. J. Cancer Chemother., 2006, vol. 33 (6), pp. 841-844.
Mokbel, Concise Notes in Oncology for MRCP and MRCS, 2005, (Radcliffe Publishing Ltd.) Drug Pharmacology and Clinical Trials, pp. 6-7.
Mononen et al., Two Percent of Finnish Prostate Cancer Patients Have a Germ-Line Mutation in the Hormone-Binding Domain of the Androgen Receptor Gene, 60(22) Cancer Research 6479-81 (2000).
Morant et al., Capecitabine in Hormone-Resistant Metastatic Prostatic Carcinoma—a Phase II Trial, Brit. J. Cancer 1312-17 (2004).
Morgan C.J., et al., "Impact of Prednisone on Toxicities and Survival in Metastatic Castration-resistant Prostate Cancer: a Systematic Review and Meta-analysis of Randomized Clinical Trials," Critical Reviews in Oncology/Hematology, Jun. 2014, vol. 90 (3), pp. 253-261.
Motzer et al., Activity of SU11248, a Multitargeted Inhibitor of Vascular Endothelial Growth Factor Receptor and Platelet-Derived Growth Factor Receptor, in Patients with Metastatic Renal Cell Carcinoma, 24(1), J. Clin. Oncol. 16-24 (2006).

(56) References Cited

OTHER PUBLICATIONS

Moul, The Evolving Definition of Advanced Prostate Cancer, Rev. Urol. S10-S17 (2004).
Mubiru et al., Nonhuman Primates as Models for Studies of Prostate Specific Antigen and Prostatic Diseases, 68(14) Prostate 1-16 (2008).
Mulcahy, Phase 3 Trial of Immunotherapy for Metastatic Prostate Cancer Terminated, Medscape Medical News, Oct. 17, 2009, [retrieved on Jun. 26, 2014] Retrieved from the internet: (URL: http://www.medscape.com/viewarticle/582220).
Mylan Petition for Inter Partes Review of U.S. Pat. No. 8,927,592, pp. 1-65 with Exhibit 1002 (Declaration of Dr. Rahul Seth,) 2016, pp. 1-109.
Nagore et al., Antineoplastic Therapy-Induced Palmar Plantar Erythrodysesthesia ('Hand-Foot') Syndrome, Incidence, Recognition and Management, 1(4) Am. J. Clin. Dermatol. 225-34 (2000).
National Cancer Institute, Common Terminology Criteria for Adverse Events v3.0 (Aug. 2006).
National Cancer Institute, Common Toxicity Criteria for Adverse Events v2.0 (Apr. 1999).
National Cancer Institute, Common Toxicity Criteria Manual Version 2.0 (Jun. 1, 1999).
National Comprehensive Cancer Network (NCCN Clinical Practice Guidelines in Oncology , Prostate Cancer) V.1 (2009), pp. 1-46.
National Comprehensive Cancer Network (NCCN Clinical Practice Guidelines in Oncology, Breast Cancer) V.1 (2009), pp. 1-122.
NCCN Antiemesis Guidelines, Internet Archive https://web.archive.org/web/20081001233326/http://www.nccn.org/professionals/physician_gls/PDF/antiemesis.pdf)(Oct. 1, 2008) (last accessed: Mar. 14, 2017).
NCI, NIH-Funded Study Shows Increased Survival in Men With Metastatic Prostate Cancer Who Receive Chemotherapy When Starting Hormone Therapy [retrieved on Aug. 4, 2015]. Retrieved from the Internet: (URL: http://www.nih.gov/news/health/dec2013/nci-05.htm).
New Hope in Advanced Prostate Cancer Alberta Saskatchewan and Ontario Fund Coverage for Jevtana (Cabazitaxel), Retrieved from the internet on Dec. 22, 2016 at https://www.newswire.ca/news-releases/new-hope-in-advanced-prostate-cancer-alberta-saskatchewan-and-ontario-fund-coverage-for-jevtana-cabazitaxel-510872201.html.
Newman S.P., et al., "The Therapeutic Potential of a Series of Orally Bioavailable Anti-angiogenic Microtubule Disruptors as Therapy for Hormone-independent Prostate and Breast Cancers," British Journal of Cancer, Dec. 2007, vol. 97 (12), pp. 1673-1682.
Nexavar (sorafenib) Label (Nov. 2007).
Niho et al., First-Line Single Agent Treatment with Gefitinib in Patients with Advanced Non-Small-Cell Lung Cancer: A Phase II Study, 24(1) J. Clin. Oncol. 64-69 (2006).
Nobili S.,et al., "Pharmacological Strategies for Overcoming Multidrug Resistance, " Current Drug Targets, 2006, vol. 7 (7), pp. 861-879.
Non-Final Office Action dated Apr. 16, 2014 for U.S. Appl. No. 13/456,720, filed Apr. 26, 2012.
Non-Final Office Action dated Jan. 16, 2013 for U.S. Appl. No. 13/456,720, filed Apr. 26, 2012.
Normanno, N., et al., "Target-based Therapies in Breast Cancer: Current Status and Future Perspectives," Endocrine-Related Cancer, Sep. 2009, vol. 16 (3), pp. 675-702.
Notice of Allowance dated Aug. 4, 2014 for U.S. Appl. No. 13/456,720, filed Apr. 26, 2012.
Notice of Allowance dated Nov. 14, 2014 for U.S. Appl. No. 13/456,720, filed Apr. 26, 2012.
NOVACEA, Inc, SEC Form 8-K at 1.02, 2008 [retrieved on Jun. 27, 2014] Retrieved from the Internet: (URL: http:/www.sec.gov/Archives/edgar/data/1178711/000119312508077953/d8k.htm).
Novantrone Gets FDA Nod for Use in Advanced Prostate Cancer, Cancer Network (Dec. 1, 1996), http://www.cancernetwork.com/articles/novantrone-gets-fda-nod-use-advanced-prostate-cancer, retrieved on Dec. 22, 2016.
Novantrone (mitoxantrone) Prescribing information (Label), 2012, pp. 1-37.
Novantrone (mitoxantrone) Label (Aug. 2008).
Numata K., et al., "The Preliminary Results of Docetaxel-Prednisolone Combination Therapy for the Japanese Patients with Hormone-Refractory Prostate Cancer," Acta Urol. Jpn., 2007, vol. 53 (2), pp. 93-97.
Numata K., et al., Urological Bulletin, 2007, vol. 53 (2), pp. 93-96.
Omlin et al., Analysis of Side Effect Profile of Alopecia, Nail Changes, Peripheral Neuropathy, and Dysgeusia in Prostate Cancer Patients Treated With Docetaxel and Cabazitaxel, 13(4) Clin. Genitourin. Cancer 1-4 (2015).
Opposition ALAFAR (Nov. 2012): Index Merck 14th. Merck & Co. USA. NI, 2006. No. 0000190 (ALAFAR refers to a specific compound, which is agomelatine).
Oudard, et al., Cabazitaxel Plus Prednisone/Prednisolone Significantly Increases Overall Survival Compared to Mitoxantrone Plus Prednisone/Prednisolone in Patients With Metastatic Castration-Resistant Prostate Cancer (MCRPC) Previously Treated With Docetaxel: Final Results With Updated Overall Survival of a Multinational Phase III Trial (TROPIC), Ann. of Oncology, 2010, vol. 21, (Suppl. 8), pp. viii272, Abstract 871PD.
Oudard S., et al., "Multicenter Randomized Phase II Study of Two Schedules of Docetaxel, Estramustine, and Prednisone Versus Mitoxantrone Plus Prednisone in Patients With Metastatic Hormone-refractory Prostate Cancer," Journal of Clinical Oncology, May 2005, vol. 23 (15), pp. 3343-3351.
Padhani, et al., The RECIST Criteria: Implications for Diagnostic Radiologists, Br. J. Radiol. 983-86 (2001).
Pal S.K., et al., "Critical Appraisal of Cabazitaxel in the Management of Advanced Prostate Cancer," Clinical Interventions in Aging, 2010, vol. 5, pp. 395-402.
Parkin D.M., et al., "Global Cancer Statistics, 2002," Ca: A Cancer Journal for Clinicians, 2005, vol. 55 (2), pp. 74-108.
Passalacqua et al., The Clinical Safety of H1-Receptor Antagonists, An EAACI Position Paper, Allergy 666-75 (1996).
Pazdur, Endpoints for Assessing Drug Activity in Clinical Trials, 13(suppl 2) The Oncologist 19-21 (2008).
Pazdur R., et al., "The Taxoids: Paclitaxel (Taxol) and Docetaxel (Taxotere)," Cancer Treatment Reviews, Oct. 1993, vol. 19 (4), pp. 351-386.
PDR Medical Dictionary at 102, 416 (2d ed. 2000).
Perez-Soler et al., Determinants of Tumor Response and Survival with Erlotinib in Patients with Non-Small-Cell Lung Cancer, 22(16) J. Clin. Oncol. 3238-47 (2004).
Perjeta (pertuzumab) Label Jun. 2012.
Petitioner's Opposition to Patent owner's Motion to Amend under 37 CFR 42.121 as submitted in U.S. Patent and Trademark Office before the Patent Trial and Appeal Board case IPR2016-00712, U.S. Pat. No. 8,927,592, dated Mar. 14, 2017.
Petitioner's Reply as submitted in U.S. Patent and Trademark Office before the Patent Trial and Appeal Board case IPR2016-00712, U.S. Pat. No. 8,927,592, dated Mar. 14, 2017.
Petrylak, D.P., et al., 'A Phase 3 Study to Evaluate the Efficacy and Safety of Docetaxel and Prednisone (DP) with or without Lenalidomide (LEN) in Patients with Castrate-Resistant Prostate Cancer (CRPC): The Mainsail Trial,' Annals of Oncology, Abstract LBA24 from Abstract Book of 37th European Society for Medical Oncology Congress Vienna, Austria, vol. 23, Suppl. 9, 2012.
Phase III Trial, NCI Dictionary of Cancer Terms, Retrieved from cancer.gov, [retrieved on Apr. 2, 2015].
Pienta K.J., et al., "Advances in Prostate Cancer Chemotherapy: A New Era Begins," CA a Cancer Journal for Clinicians, 2005, vol. 55 (5), pp. 300-318 and 323-325.
Pivot, et al., Inpharma, Abstract 1659 (Oct. 11, 2008).
Pivot X., et al. , "Multicenter Phase 2 Study of XRP6258 in Taxane Resistant Metastatic Breast Cancer (MBC) Patients (pts)," Breast Cancer Research and Treatment, 2005, vol. 94 (1), pp. S68, Abstract 138.
Pouessel D., et al., "Actualities in Prostate Cancer in ASCO Annual Meeting 2010," Bulletin Du Cancer, 2010, vol. 97 (12), pp. 1563-1572.
Prednisone Label (Apr. 2008).

(56) References Cited

OTHER PUBLICATIONS

Press Release: OncoGenex Announces Top Line Survival Results of Phase 3 SYNERGY Trial Evaluating Custirsen for Metastatic Castration-Resistant, Prostate Cancer, PRNewswire Apr. 28, 2014.
Press Release Roche Provides Update on Phase III Study of Avastin in Men with Late Stage Prostate Cancer, Media Release Mar. 12, 2010 [retrieved on Jun. 27, 2014] Retrieved from the Internet: (URL: http://www.roche.com/media/media_releases/med-cor-2010-03-12.htm.).
Press Release: Takeda Announces Termination of Orteronel (TAK-700) Development for Prostate Cancer in Japan., U.S.A. and Europe, Jun. 19, 2014 [retrieved on Jun. 27, 2014] Retrieved from the Internet: (URL: http://www.takeda.com/news/2014/20140619_6615.html).
Process 06-IP-89, Retrieved from the internet : URL: (http://intranet.comunidadandina.org/Documentos/Procesos/209-IP-2005.doc); and Process 36-IP-2004 (http://www.notinet.com.co/serverfiles/servicios/archivos/30jul04/ca36-04.htm).
Prostate Cancer Treatment, Jevatana (cabazitaxel) Injection, Retrieved from the internet on Dec. 19, 2016 at http://www.jevtana.com/treatment.
PROVENGE (sipuleucel-T) Label, 2010.
Sharom, F.J., "ABC Multidrug Transporters: Structure, Function and Role in Chemoresistance," Pharmacogenomics, Jan. 2008, vol. 9 (1), pp. 105-127.
Tannock, et al., Docetaxel Plus Prednisone Improves Survival in Men With Advanced Prostate Cancer, Cancer Treatment Reviews, (2005), vol. 31. pp. 403-407.
Quinn et al., Docetaxel and Atrasentan Versus Docetaxel and Placebo for Men with Advanced Castration-Resistant Prostate Cancer (SWOG S0421): A Randomized Phase 3 Trial, Lancet 893-900 (2013).
Ramanathan et al.,, "A Phase II Study of Milataxel: A Novel Taxane Analogue in Previously Treated Patients With Advanced Colorectal Cancer," Cancer Chemotherapy and Pharmacology, 2008, vol. 61 (3), pp. 453-458.
Ramiah V., et al., "Clinical Endpoints for Drug Development in Prostate Cancer," Current Opinion in Urology, 2008, vol. 18 (3), pp. 303-308.
Random House Webster's College Dictionary, 2001 Second Revised and Updated Random House Edition (2003), p. 1393.
Ratain and Sargent, Optimising the Design of Phase II Oncology Trials: The Importance of Randomisation, Eur. J. Cancer 275-280 (2009).
Ratain M.J., et al., "Critical Role of Phase I Clinical Trials in Cancer Treatment. American Society of Clinical Oncology," Journal of Clinical Oncology, Feb. 1997, vol. 15 (2), pp. 853-859.
Ratain M.J., Phase II Oncology Trials: Let's Be Positive, Clinical Cancer Research, Aug. 2005 vol. 11 (16), pp. 5661-5662.
Ratain, M.J. et al., Statistical and Ethical Issues in the Design and Conduct of Phase I and II Clinical Trials of New Anticancer Agents, 85(20) J. Nat'l Cancer Inst. 1637-43 (1993) .
Reck et al., An Open-Label, Multi Centre, Phase II, Non-Comparative Trial of ZD1839 Monotherapy in Chemotherapy-Naive Patients with Stage IV or Stage III Non-Operable Non-Small Cell Lung Cancer (NSCLC), 23(16S) J. Clin. Oncol. 7098 (2005).
Reese et al., A Phase II Trial of Irinotecan in Hormone-Refractory Prostate Cancer, 16(4) Investig. New Drugs 353-59 (1999).
Revision Sistematica y Modelo Economico de Efectividad Glinica y Goste•Efectividad de Docetaxel en Combinacion con Prednisona/ Prednisolona para el Tratamiento de Cancer de Prostata Metastasico Refradario a Homonas. [Retrieved from the internet on Jul. 29, 2014]. Retrieved from the internet:( URL: http://www.sefh.es/sefhboletin/vernoticiaboletin.php?id=2663).
Richards L., et al., "Improved Survival in Second-Line Advanced Prostate Cancer Treated with Cabazitaxel," Nature Reviews Clinical Oncology, 2010, vol. 7 (12), p. 671.
Risbridger G.P., et al., "Breast and Prostate Cancer: More Similar than Different," Nature Reviews Cancer, Mar. 2010, vol. 10 (3), pp. 205-212.
Risinger A.L., et al., "The Taccalonolides: Microtubule Stabilizers That Circumvent Clinically Relevant Taxane Resistance Mechanisms," Cancer Research, Nov. 2008, vol. 68 (21), pp. 8881-8888.
Rodrigues G., et al., "Open Clinical Uro-Oncology Trials in Canada," The Canadian Journal of Urology, 2007, vol. 14 (6), pp. 3779-3786.
Rosenberg et al., Activity of Second-Line Chemotherapy in Docetaxel-Refractory Hormone-Refractory Prostate Cancer Patients, Randomized Phase 2 Study of Ixabepilone or Mitoxantrone and Prednisone, 110(3) Cancer 556-63 (2007).
Ross R.W., et al., "Inherited Variation in the Androgen Pathway Is Associated With the Efficacy of Androgen-deprivation Therapy in Men With Prostate Cancer," Journal of Clinical Oncology, Feb. 2008, vol. 26 (6), pp. 842-847.
Rothenstein J.M., et al., "Company Stock Prices Before and After Public Announcements Related to Oncology Drugs," Journal of the National Cancer Institute, Oct. 2011, vol. 103 (20), pp. 1507-1512.
Saad et al., Randomized Phase II Trial of Custirsen (OGX-011) in Combination with Docetaxel or Mitoxantrone as Second-Line Therapy in Patients with Metastatic Castrate-Resistant Prostate Cancer Progressing After First-Line Docetaxel: CUOG Trial P-06c, 17(17) Clin. Cancer Res. 5765-73 (2011).
Sandoz Inc.'s Detailed Statement of the Factual and Legal Bases for Its Opinion That U.S. Pat. Nos. 5,847,170, 7,241,907 & 8,927,592 Are Invalid, Unenforceable and/or Not Infringed by the Manufacture, Use, Importation, Sale or Offer for Sale of the Sandoz Product, pp. 7-18 [Redacted].
Sanofi Oncology website, Oct. 2008, pp. 1-2. Retrieved from the internet, URL: https://www.sanofi.ma/fr/nous-connaitre/solutions-de-sante/oncologie.
Sanofi-Aventis Annual Report SEC Form 20-F 2010, 335 pages.
Sanofi-Aventis Annual Report SEC Form 20-F 2011, 335 pages.
Sanofi-Aventis Annual Report SEC Form 20-F 2012, 458 pages.
Sanofi-Aventis Annual Report SEC Form 20-F 2013, 304 pages.
Sanofi-Aventis Annual Report SEC Form 20-F 2014, 413 pages.
Sanofi-Aventis Annual Report SEC Form 20-F 2015, 233 pages.
Sanofi-Aventis Annual Report SEC Form 20-F 2016—Part 1 of 4.
Sanofi-Aventis Annual Report SEC Form 20-F 2016—Part 2 of 4.
Sanofi-Aventis Annual Report SEC Form 20-F 2016—Part 3 of 4.
Sanofi-Aventis Annual Report SEC Form 20-F 2016—Part 4 of 4.
Sanofi-Aventis Annual Report SEC Form 20-F, Dec. 2006, pp. 1-301.
Sanofi-aventis Annual Report SEC Form 20-F, Dec. 2007, pp. 1-283.
Sanofi-aventis Annual Report SEC Form 20-F, Dec. 2008, pp. 1-320.
Sanofi-Aventis Annual Report SEC Form 20-F (Dec. 31, 2006) at 39, [retrieved on Jun. 27, 2014] Retrieved from the internet: (URL: http://www.sec.gov/Archives/edgar/data/1121404/000119312507072848/d20f.htm).
Sanofi-Aventis Annual Review, 2008, pp. 1-28, URL: https://ddd.uab.cat/pub/infanu/34542/iaSANAVEa2008ieng.pdf.
Sanofi-Aventis Press Release: EPS Growth in Q2 2010, (Jul. 29, 2010), pp. 1-27.
Sanofi-Aventis Press Release, Jevtana (cabazitaxel) Injection Now Available in the U.S., (Jul. 19, 2010).
Sanofi-Aventis Press Release: "Phase III Data Showing Improved Survival with Jevtana® (cabazitaxel) injection in Second-Line Advanced Prostate Cancer Published in the Lancet,", retrieved on Oct. 30, 2018 from http://www.news.sanofi.us/press-releases?item=118536&printable.
Sanofi-Aventis Press Release: Q1 2010: A Good First Quarter, (Apr. 29, 2010), pp. 1-19.
Sanofi-Aventis Press Release: Resilient Sales and Business EPS in Q3 2010, (Oct. 28, 2010), pp. 1-24.
Sanofi-Aventis Press Release: Sanofi-Aventis Delivers 2008 Results Above Guidance, Feb. 11, 2009, pp. 1-27.
Sanofi-Aventis Press Release: Sanofi•Aventis Delivers Double-Digit EPS Growth in 2009 as the Transformation Program Progresses, Feb. 10, 2010, pp. 1-26.
Sartor et al., Cabazitaxel vs. Docetaxel in Chemotherapy-Naïve (CN) Patients with Metastatic Castration-Resistant Prostate Cancer (mCRPC): A Three Arm Phase III Study (FIRSTANA), J. Clin. Oncol. Abstr. 5006 (2016).

(56) References Cited

OTHER PUBLICATIONS

Sartor O., et al., "Cabazitaxel vs docetaxel in chemotherapy-naïve patients with metastatic castration-resistant prostate cancer: A three-arm phase III study (FIRSTANA)," ASCO Annual meeting 2016, slides 1-22.
Sartor O., et al., "Improving Outcomes with Recent Advances in Chemotherapy for Castrate-Resistant Prostate Cancer," Clinical Genitourinary Cancer, 2010, vol. 8 (1), pp. 23-28.
Sartor O., et al., "Novel Therapeutic Strategies for Metastatic Prostate Cancer in the Post-Docetaxel Setting," The Oncologist, Nov. 2011, vol. 16 (11), pp. 1487-1497.
Sartor O., "State-of-the-Art Management for the Patient with Castration-Resistant Prostate Cancer in 2012," American Society of Clinical Oncology Educational Book, Jan. 2012, vol. 32, pp. 289-291.
Sessa et al., Phase I Clinical and Pharmacokinetic Studies of the Taxoid Derivative RPR 109881A Administered as a 1-Hour or 3-Hour Infusion in Patients with Advanced Solid Tumors, Annals of Oncol. 1140-50 (2002).
Sessa et al., Phase I Clinical and Pharmacokinetic Study of the Oral Platinum Analogue JM216 Given Daily for 14 Days, Annals of Oncol. 1315-22 (1998).
Shabafrouz K., et al., "New Drugs at the Horizon for Men with Prostate Cancer," Revue Medicale Suisse, 2010, vol. 6 (250), pp. 1057-1058 and 1060-1061.
Sheiner L.B., "Learning versus confirming in clinical drug development," Clinical Pharmacology & Therapeutics, Mar. 1997, vol. 61(3), pp. 275-291.
Shelley M., et al., "Docetaxel Plus Prednisone Improves Survival in Men with Advanced Prostate Cancer," Cancer Treatment Reviews, 2005, vol. 31 (5), pp. 403-407.
Shepard D.R., et al., "Estimation of the Effect of Food on the Disposition of Oral 5-Fluorouracil in Combination with Eniluracil," Cancer Chemotherapy and Pharmacology, May 2002, vol. 49(5), pp. 398-402.
Shimazui T., et al., "Three-Weekly Docetaxel with Prednisone is Feasible for Japanese Patients with Hormone-Refractory Prostate Cancer: A Retrospective Comparative Study with Weekly Docetaxel Alone," Journal of Clinical Oncology, 2007, vol. 37 (8), pp. 603-608.
Signs and Symptoms of Prostate Cancer, American Cancer Society, Retrieved from the internet on Nov. 19, 2016 at http://www.cancer.org/cancer/prostatecancer/detailedguide/prostate-cancer-signs-symptoms.
Singh A.K., et al., "Interpreting Results of Clinical Trials: A Conceptual Framework," Clinical Journal of the American Society of Nephrology, Sep. 2008, vol. 3(5), pp. 1246-1252.
Slovin S.F., et al., "Ipilimumab Alone or in Combination with Radiotherapy in Metastatic Castration-Resistant Prostate Cancer: Results from an Open-Label, Multicenter Phase I/II Study," Annals of Oncology, 2013, vol. 24 (7), pp. 1813-1821.
Small E., et al., "Randomized Phase II Study Comparing 4 Monthly Doses of Ipilimumab (MDX-010) as a Single Agent or in Combination with a Single Dose of Docetaxel in Patients with Hormone-Refractory Prostate Cancer," Journal of Clinical Oncology (Meeting Abstracts), 2006, vol. 24 (18S), pp. S4609.
Small E.J., et al., "Granulocyte Macrophage Colony Stimulating Factor-Secreting Allogeneic Cellular Immunotherapy for Hormone-Refractory Prostate Cancer," Clinical Cancer Research, 2007, vol. 13, pp. 3883-3891.
Small E.J., et al., "Randomized Study of Three Different Doses of Suramin Administered with a Fixed Dosing Schedule in Patients with Advanced Prostate Cancer: Results of Intergroup 0159, Cancer and Leukemia Group B 9480," Journal of Clinical Oncology, Aug. 2002, vol. 20(16), pp. 3369-3375.
Small et al., A Phase II Trial of Gefitinib in Patients with Non-Metastatic Hormone-Refractory Prostate Cancer, 100 BJU Int'l. 765-69 (2007).
Sonpavde et al., Sunitinib Malate for Metastatic Castration-Resistant Prostate Cancer Following Docetaxel-Based Chemotherapy, 21(2) Ann. Oncol. 319-24 (2010).

Gottesman M.M., "Mechanisms of Cancer Drug Resistance," Annual Review of Medicine, Feb. 2002, vol. 53, pp. 615-627.
MSN's Detailed Statement of the Factual and Legal Bases for Its Opinion That U.S. Pat. No. 8,927,592 B2 Is Invalid, pp. 9-29 [Redacted].
Spigel D.R., 'Single-Agent Gefitinib in Patients with Untreated Advanced Non-Small-Cell Lung Cancer and Poor Performance Status: A Minnie Pearl Cancer Research Network Phase II Trial,' Clinical Lung Cancer, vol. 7, No. 2, pp. 127-132 (2005).
Stedman's Medical Dictionary, pp. 168, 360, 376, 537, and 1215, 27th Edition, 2000.
Sternberg C.N., et al., "Larotaxel with Cisplatin in the First-Line Treatment of Locally Advanced/Metastatic Urothelial Tract or Bladder Cancer: A Randomized, Active-Controlled, Phase III Trial (Cilab)," Oncology, 2013, vol. 85 (4), pp. 208-215.
Straub et al., Intravenous Hydrophobic Drug Delivery: A Porous Particle Formulation of Paclitaxel (AI-850), 22(3) Pharm. Res. 347-55 (2005).
Sullivan P.W., et al., "Quality of Life as a Potential Predictor for Morbidity and Mortality in Patients with Metastatic Hormone-Refractory Prostate Cancer," Quality of Life Research, Oct. 2006, vol. 15(8), pp. 1297-1306.
Susman, Asgo: Calcitriol Fails in ASCENT-2 Prostate CA Trial, MedPage Today, Jun. 9, 2010 [retrieved on Jun. 27, 2014], Retrieved from the Internet:(URL:http://www.medpagetoday.com/MeetingCoverage/ASC0/20575).
Sutent (sunitinib malate) Label (Apr. 2008).
Szmulewitz R.Z., et al., "Playing Russian Roulette with Tyrosine Kinase Inhibitors," Clinical Pharmacology & Therapeutics, 2013, vol. 93(3), pp. 242-244.
Takeda M., et al., "The Establishment of two Paclitaxel Resistant Cancer Cell Lines and the Mechanism of Paclitaxel Resistance With Two Cell Lines," The Prostate, 2007, vol. 67 (9), pp. 955-967.
Tan, "Novel Agents in the Treatment of Hormone-Independent Metastatic Prostate Cancer," Actas Urológicas Españolas, 2007, vol. 31 (6), pp. 660-685 (followed by English translation).
Tannock I., et al., "Treatment of Metastatic Prostatic Cancer with Low-Dose Prednisone: Evaluation of Pain and Quality of Life as Pragmatic Indices of Response," Journal of Clinical Oncology, 1989, vol. 7 (5), pp. 590-597.
Tannock I.F., et al., "Chemotherapy with Mitoxantrone Plus Prednisone or Prednisone Alone for Symptomatic Hormone-Resistant Prostate Cancer: A Canadian Randomized Trial with Palliative End Points," Journal of Clinical Oncology, 1996, vol. 14 (6), pp. 1756-1764.
Tarceva (erlotinib) Label (Apr. 2009).
Taxotere (Docetaxel) mejora significativamente la supervivencia de los pacientes con cancer de prostata avanzado. Retrieved from the Internet: (URL: http://www.pmfarma.es/noticias/7074-taxotere-docetaxelmejora-significativamente-la-supervivencia-de-los-pacientes-con-cancer-de-prostataavanzado).
Taxotere (Docetaxel) Significantly Improves the Survival of Patients With Advanced Prostate Cancer, Feb. 2007, sanofi-aventis Press Release; pp. 1-4.
Taxotere Patient Information Leaflet and Prescribing Information (Label), May 2004, pp. 1-35.
Taxotere Patient Information Leaflet and Prescribing Information (Label), Oct. 2006, pp. 1-55.
Taxotere Prescribing Information (Label), Sep. 2007, pp. 1-57.
Taylor B.S., et al., "Integrative Genomic Profiling of Human Prostate Cancer," Cancer cell, 2010, vol. 18(1), pp. 11-22.
Ten Tije et al., Pharmacological Effects of Formulation Vehicles: Implications for Cancer Chemotherapy, 42(7) Clin. Pharmacokinet. 665-85 (2003).
The National Horizon Scanning Centre of National Institute for Health Research, Cabazitaxel (XRP-6258) for Hormone Refractory, 2009, Metastatic Prostate Cancer—Second line After Docataxel, University of Birmingham, pp. 1-6.
Torisel (temsirolimus) Label (May 2007).
Trudeau, et al., Docetaxel in Patients with Metastatic Breast Cancer: A Phase II Study of the National Cancer Institute of Canada—Clinical Trials Group, J. Clin. Oncol., 422-428 (1996).

(56) References Cited

OTHER PUBLICATIONS

Tufts Cost Study as retrieved on Feb. 1, 2017 from http://csdd.tufts.edu/news/complete_story/pr_tufts_csdd_2014_cost_study, pp. 1-3, 2014.
Un farmaco contra el cancer de prostata demuestra una alta eficacia. Retrieved from the internet: (URL: http://www.dimedicina.com/enfermedades/urologicas/actualidad/un-farmaco-contra-elcancer-de-prostata-demuestra-una-alta-eficacia).
Undevia S.D., et al., "Pharmacokinetic Variability of Anticancer Agents," Nature Reviews Cancer, Jun. 2005, vol. 5 (6), pp. 447-458.
Van Cutsem., et al., A Phase III Study Comparing Larotaxel to 5-FU (Continuous Intravenous 5-FU or Capecitabine) in Patients with Advanced Pancreatic Cancer (APC) Previously Treated with a Gemcitabine Containing Regimen, 21(6S) Annals of Oncol. Oral Presentations, O-0007, Jul. 2010.
Van Hook K., et al., "Orteronel for the Treatment of Prostate Cancer," Future Oncology, 2014, vol. 10 (5), pp. 803-811.
Van Ruitenbeek P., et al., 'Histamine H1-receptor blockade in humans affects psychomotor performance but not memory,' Journal of psychopharmacology, vol. 22 No. 6, pp. 663-672 (2008).
Van Tellingen, O., et al., "Cremophor EL Causes (pseudo-) Non-Linear Pharmacokinetics of Paclitaxel in Patients," British Journal of Cancer, Sep. 1999, vol. 81 (2), pp. 330-335.
Verweij, et al., Paclitaxel (Taxol) and Docetaxel (Taxotere): Not Simply Two of a Kind, Ann. Oncol. 495-505 (1994).
View of NCT00417079 on 2008_08_31-XRP6258 Plus Predisone Compared to Mitoxantrone Plus Prednisone in Hormone Refractory Metasiattc Prostate Cancer, (retrieved on Apr. 6, 2015). Retrieved from the internet: (URL: https://clinicaltrials.gov/archive/NCT00417079/2008_08_31).
Vogel et al., Efficacy and Safety of Trastuzumab as a Single Agent in First-Line Treatment of HER2-Overexpressing Metastatic Breast Cancer, 20(3) J. Clin. Oncol. 719-26 (2002).
Vogelzang N.J., et al., "A Phase II Trial of Suramin Monthly x 3 for Hormone-Refractory Prostate Carcinoma," Cancer, 2003, vol. 100 (1), pp. 65-71.
Von Hoff D.D and Turner J., "Response Rates, Duration of Response, and Dose Response Effects in Phase I Studies of Antineoplastics," Investigational New Drugs, Feb. 1991, vol. 9 (1), pp. 115-122.
Vrignaud et al., Preclinical Antitumor Activity of Cabazitaxel, a Semisynthetic Taxane Active in Taxane-Resistant Tumors, 19(11) Clin. Cancer Res. 2973-83 (2013).
Vrignaud et al., Preclinical Profile of Cabazitaxel, Drug Des. Devel. & Ther. 1851-67 (2014).
Wazana, Physicians and the Pharmaceutical Industry: Is a Gift Ever Just a Gift?, JAMA 283 (2000) 373-380.
What is Prostate Cancer?, Jevatana (cabazitaxel) Injection, Retrieved from the internet on Sep. 19, 2016 at http://www.jevtana.com/what-is-prostate-cancer.
What is PROVENGE Immunotherapy?, Retrieved from the internet on Oct. 5, 2016 at http://www.provenge.com/advanced-prostate-cancer-immunotherapy.aspx.
Why ZYTIGA? (abiraterone acetate), Retrieved from the internet on Oct. 6, 2016 at https://www.zytigo.com/about-zytigo/why-zytiga.
Wiechec E., et al., "The Effect of Genetic Variability on Drug Response in Convention Breast Cancer Treatment," European Journal of Pharmacology, 2009, vol. 625 (1-3), pp. 122-130.
Williams R., 'Discontinued drugs in 2007: oncology drugs,' Expert Opinion Investig. Drugs, vol. 17 No. 12, pp. 1791-1816, (2008).
Williams R., et al., "Discontinued Drugs in 2008: Oncology Drugs," Expert Opinion on Investigational Drugs, 2009, vol. 18 (11), pp. 1581-1594.

Wils, P., et al., "Polarized transport of docetaxel and vinblastine mediated by Pglycoprotein in human intestinal epithelial cell monolayers," Biochemical Pharmacology, 48(7):1528-30 (1994).
Wirth, et al., "The Antiandrogen Withdrawal Syndrome," Urol. Res., 1997, 25 (Suppl. 2), pp. S67-S71.
Wirth M.P, "Hormone-refractory Prostate Cancer: What Have We Learned?," BJU International, Jul. 2007, vol. 100 (Suppl 2), pp. 56-59.
World Health Organization WHO Handbook for Reporting Results of Cancer Treatment, Geneva, 1979, pp. 1-46.
Xeloda (capecitabine) Label Feb. 2003.
XOFIGO (radium Ra 223 dichloride) Label (May 2013).
Xtandi Clinical Trials & Results, How Xtandi May Help, Retrieved from the internet on Oct. 6, 2016 at https://www.xtandi.com/xtandi-clinical-trials.
Xtandi (enzalutamide) Label (Aug. 2012).
Yervoy (ipilimumab), Prescribing Information (Label), Dec. 2013.
Yoo G.H., et al., "XRP6258-Induced Gene Expression Patterns in Head and Neck Cancer Carcinoma," The Laryngoscope, 2010, vol. 120 (6), pp. 1114-1119.
Zatloukal P., et al., "Randomized Multicenter Phase II Study of Larotaxel (XRP9881) in Combination with Cisplatin or Gemcitabine as First-Line Chemotherapy in Nonirradiable Stage IIIB or Stage IV Non-Small Cell Lung Cancer," Journal of Thoracic Oncology, 2008, vol. 3(8), pp. 894-901.
Zhu, et al., Does "Clock" Matter in Prostate Cancer, Cancer Epidemiol. Biomarkers Prev. 3-5 (2006).
Ziada et al., The Use of Trastuzumab in the Treatment of Hormone Refractory Prostate Cancer; Phase II Trial, 60(4) The Prostate 332-37 (2004).
Zielinski A., et al., "Custirsen (OGX-011): a Second-Generation Antisense Inhibitor of Clusterin in Development for the Treatment of Prostate Cancer," Future Oncology, 2012, vol. 8 (10), pp. 1239-1251.
Zytiga (abiraterone acetate) Label (Apr. 2011).
*Sanofi Mature IP* v. *Mylan Laboratories Limited*, Case No. 2018-1203, United States Court of Appeals for the Federal Circuit, Appeal from the United States Patent and Trademark Office, Patent Trial and Appeal Board in No. IPR2016-00712, Decision dated Feb. 5, 2019, 12 pages.
Lenz, H.J., Management and Preparedness for Infusion and Hypersensitivity Reactions, The Oncologist, 12:601-609, 2007.
R008407, Non Final Office Action issued by the U.S. Patent and Trademark Office in U.S. Appl. No. 16/251,143, filed Jan. 18, 2019, dated Mar. 1, 2019.
R008406, Patent Owner's Responsive Brief on the Effect of the CAFC Decision on Patent Owner's Motion to Amend as submitted in the U.S. Patent and Trademark Office before the Patent Trial and Appeal Board Case IPR2016-00712, U.S. Pat. No. 8,927,592, dated Jun. 7, 2019, 30 pages.
R008408, Petitioner Mylan's Reply Brief on Remand Pursuant to Paper No. 108 as submitted in the U.S. Patent and Trademark Office before the Patent Trial and Appeal Board Case IPR2016-00712,U.S. Pat. No. 8,927,592, dated Jun. 21, 2019, 12 pages.
R008409, Final Written Decision on Remand issued in the Patent Trial and Appeal Board Case IPR2016-00712,U.S. Pat. No. 8,927,592 dated Oct. 22, 2019.
R008410, Final Rejection issued by the U.S. Patent and Trademark Office in U.S. Appl. No. 16/251,143, filed Jan. 18, 2019, dated Aug. 12, 2019.

* cited by examiner

ANTITUMORAL USE OF CABAZITAXEL

CROSS-REFERENCE TO RELATED APPLICATIONS

This application is a continuation of U.S. application Ser. No. 14/575,566, filed Dec. 18, 2014, which is a continuation of U.S. application Ser. No. 13/456,720, filed Apr. 26, 2012, which is a continuation of International Application No. PCT/IB2010/054866, filed Oct. 27, 2010, which claims the benefit of priority of U.S. Provisional Application No. 61/256,160, filed Oct. 29, 2009, U.S. Provisional Application No. 61/293,903, filed Jan. 11, 2010, U.S. Provisional Application No. 61/355,834, filed Jun. 17, 2010, U.S. Provisional Application No. 61/355,888, filed Jun. 17, 2010, U.S. Provisional Application No. 61/369,929, filed Aug. 2, 2010, U.S. Provisional Application No. 61/383,933, filed Sep. 17, 2010, and U.S. Provisional Application No. 61/389,969, filed Oct. 5, 2010, all of which are incorporated herein by reference.

The present invention relates to a novel antitumoral use of cabazitaxel in the treatment of prostate cancer, which may be metastatic, especially for patients who are not catered for by a taxane-based treatment. In particular, the present invention relates to the use of cabazitaxel in the treatment of patients with castration resistant metastatic prostate cancer, who have been previously treated with a docetaxel based regimen, an unmet medical need.

BACKGROUND

Prostate cancer affects a large proportion of the male population worldwide: 680 000 cases worldwide in 2002; it is predicted that there will be 900 000 new cases per year up to 2010 (CA Cancer J. Clin., 2005, 55, 74-108). It is the most frequently occurring cancer in men after lung cancer.

Prostate cancer is generally treated at the start by depriving the androgenic hormones, i.e. by surgical excision of the testicles The Current State of Hormonal Therapy for Prostate Cancer CA Cancer J. Clin., May 2002; 52: 154-179, or by radiotherapy treatment External beam radiation therapy for prostate cancer CA Cancer J. Clin., November 2000; 50: 349-375. Treatments with antiandrogens or hormone manipulations are associated with responses of short duration and without any improvement in the survival time.

The use of cytotoxic chemotherapy is not a routine treatment, whereas its role in alleviating the symptoms and reducing the levels of PSA (prostate-specific antigen) is established. No monotherapy has obtained a degree of response of greater than 30%; combinations with an effect on PSA levels were tested. No effect on the survival time was seen and, what is more, the toxicity of these treatments, particularly on elderly patients, is problematic since, in addition to their tumour, they are generally suffering from related health problems and have a limited reserve of bone marrow.

Until recently, the chemotherapies used were limited to cyclophosphamide, anthracyclines (doxorubicin or mitoxantrone) and estramustine, and the effects of these treatments are relatively mediocre. Palliative effects were observed in patients following the administration of corticoids alone or of mitoxantrone with either prednisone or hydrocortisone. Following Phase II trials, the combination of mitoxantrone with corticoids was recognized as the reference treatment for hormone-resistant prostate cancer. More recently, treatments with docetaxel in combination with estramustine or prednisone have made it possible to treat cancers that are resistant to hormone deprivation Advances in Prostate Cancer Chemotherapy: A New Era Begins CA Cancer J. Clin., September 2005; 55: 300-318, the survival was improved by 2.4 months.

It is generally accepted that the responses in advanced prostate cancers are difficult to evaluate on account of the heterogeneity of the disease and the lack of consensus regarding the treatment response criteria. Many patients with metastatic prostate cancer have no measurable disease, but have symptoms dominated by bone metastases. Measurement of the PSA level has been found to be a means for evaluating novel candidates and also the measurement of the tumour when this is possible, the measurement of bone tumours, the quality of life and the measurement of the pain.

Furthermore, cancer may become resistant to the agents used, in particular to taxanes, which limits the possible treatment options. Several taxane resistance mechanisms have been described (expression of P-glycoprotein P-gp, mdr-1 gene, modified metabolism of taxane, mutation of the tubulin gene, etc.): see Drug Resistance Updates 2001, 4(1), 3-8; J. Clin. Onc. 1999, 17(3), 1061-1070.

The technical problem that the invention intends to solve is that of providing a novel therapeutic option for treating prostate cancer, especially for patients who are not catered for by a taxane-based treatment, such as patients with castration resistant metastatic prostate cancer who have been previously treated with docetaxel (sold under the brand name Taxotere®) based regimen, an unmet medical need.

Four clinical trials on cabazitaxel are known since April 2006. Three monotherapy tests have made it possible to determine the maximum tolerated dose and the toxicities at the limit doses: these tests were performed on breast, sarcoma and prostate tumours. Doses of 10-30 mg/m$^2$ every three hours were used. A phase II trial was performed on patients with a breast cancer, who had previously received taxanes and anthracyclines as adjuvant (i.e. after a surgery) or as a first-line treatment. The response levels were 14.6% as adjuvant and 9.5% as second-line treatment.

SUMMARY

The invention relates to a novel antitumoral pharmaceutical therapeutic use comprising cabazitaxel of formula

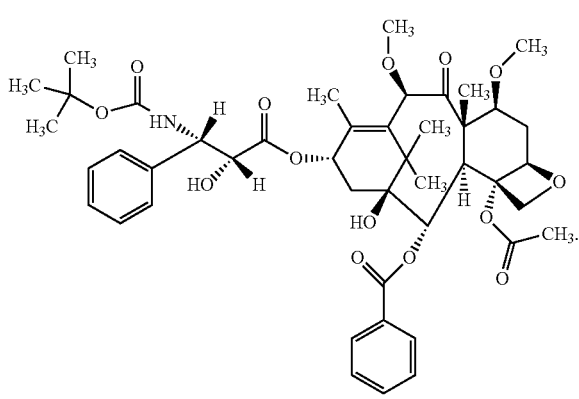 [SMILES: CO[C@H]1C(=O)[C@]2(C)[C@@H](OC)C[C@H]3OC[C@@]3(OC(C)=O)[C@H]2[C@H](OC(=O)c2ccccc2)[C@]2(O)C[C@H](OC(=O)[C@H](O)[C@@H](NC(=O)OC(C)(C)C)c3ccccc3)C(C)=C1C2(C)C]

The invention also relates to methods of treating patients with prostate cancer comprising administering an effective amount of the antitumoral agent cabazitaxel to said patient.

This antitumoral agent may be in the form of anhydrous base, a hydrate or a solvate, intended for treating prostate cancer, in particular for treating patients who are not catered for by a taxane-based treatment, such as patients who have been previously treated with a docetaxel-based regimen. This compound is preferably administered to a patient with advanced metastatic disease. In particular, the compound is administered to a patient with castration resistant prostate cancer. Cabazitaxel is preferably administered in combination with a corticoid chosen especially from prednisone and prednisolone. This corticoid is preferably administered at a daily dose of 10 mg orally.

In some aspects of the invention, cabazitaxel is administered in combination with prednisone for its use as a medicament in the treatment of patients with hormone-refractory prostate cancer who have been previously treated with docetaxel based regimen.

In some aspects of the invention, cabazitaxel is administered at a dose (defined for each administration) of between 20 and 25 mg/m². Cabazitaxel may be in the form of an acetone solvate. More particularly, the acetone solvate of cabazitaxel contains between 5% and 8% and preferably between 5% and 7% by weight of acetone.

In some aspects of the invention, cabazitaxel may be administered by intravenous infusion at a dose of between 15 and 25 mg/m², this administration cycle of the antitumour agent being repeated at an interval of 3 weeks between each cabazitaxel administration, which interval may be prolonged by 1 to 2 weeks depending on the tolerance to the preceding cabazitaxel administration.

In some embodiments, the effective amount of cabazitaxel produces at least one therapeutic effect selected from the group consisting of increase in overall survival, partial response, reduction in tumor size, reduction in metastasis, complete remission, partial remission, stable disease, or complete response.

The present invention also relates to a pharmaceutical composition that treats patients with prostate cancer comprising a clinically proven safe and effective amount of cabazitaxel.

Further embodiments of the invention comprise methods or using, treating, promoting, and providing cabazitaxel.

The present invention also relates to packages and articles of manufacture.

DETAILED DESCRIPTION

Definitions

Figure 1:
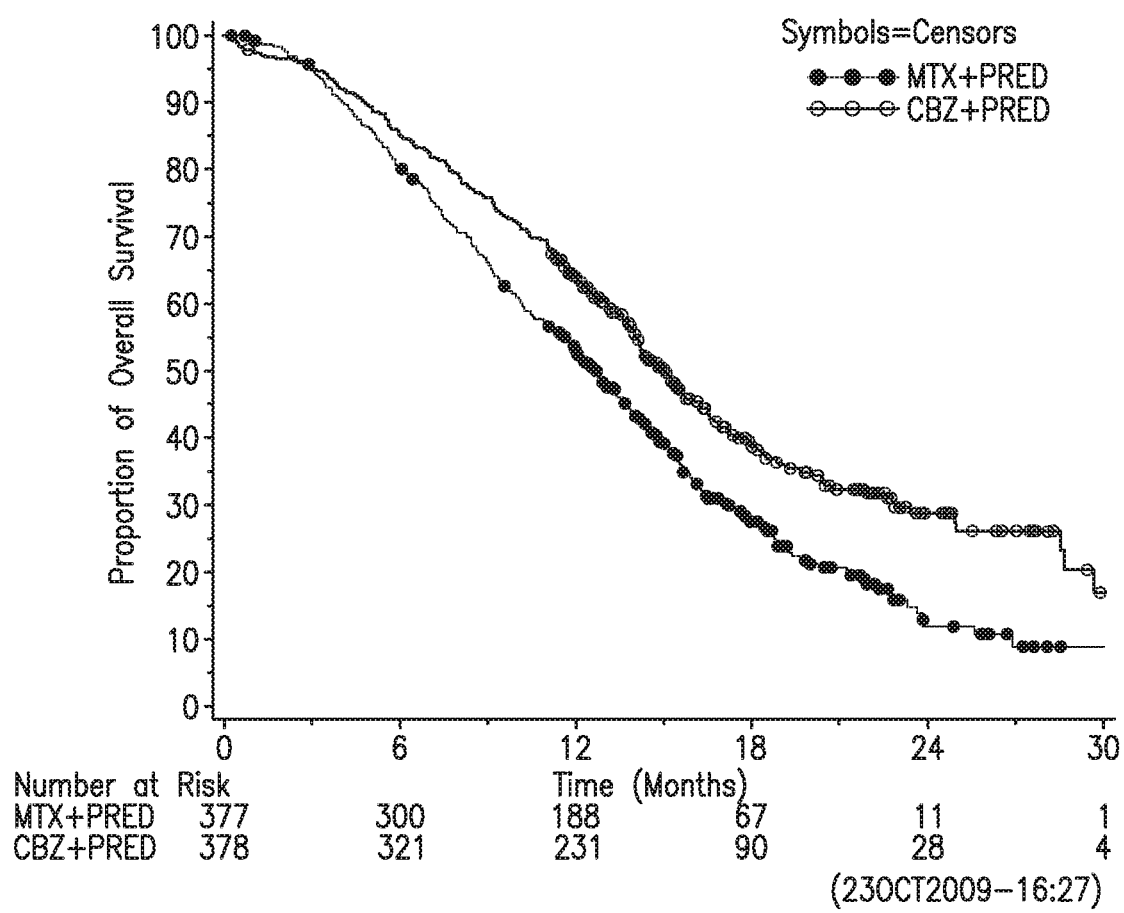
FIG. 1 displays the Kaplan-Meier curves of the overall survival in a cabazitaxel study.

Effective amount, as used herein, means an amount of a pharmaceutical compound, such as cabazitaxel, that produces an effect on the cancer to be treated.

Clinically proven, as used herein, means clinical efficacy results that are sufficient to meet FDA approval standards.

Castration resistant prostate cancer, as used herein, is synonymous with hormone-refractory prostate cancer.

"Patient," as used herein, includes both human and animals. In one embodiment, a patient is a human.

Cabazitaxel belongs to the taxoid family and has the formula:

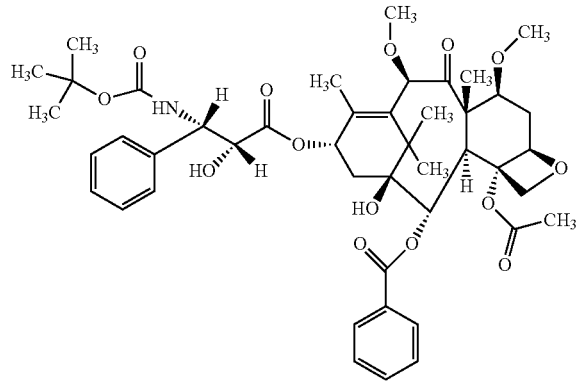 [SMILES: CO[C@H]1C(=O)[C@]2(C)[C@@H](OC)C[C@H]3OC[C@@]3(OC(C)=O)[C@H]2[C@H](OC(=O)c2ccccc2)[C@]2(O)C[C@H](OC(=O)[C@H](O)[C@@H](NC(=O)OC(C)(C)C)c3ccccc3)C(C)=C1C2(C)C]

The chemical name of cabazitaxel is 4α-acetoxy-2α-benzoyloxy-5,20-epoxy-1β-hydroxy-7β,10β-dimethoxy-9-oxo-11-taxen-13α-yl (2R,3S)-3-tert-butoxycarbonyl-amino-2-hydroxy-3-phenylpropionate. Cabazitaxel is synonymously known as (2α,5β,7β, 10β,13α)-4-acetoxy-13-({(2R,3S)-3-[(tertbutoxycarbonyl)amino]-2-hydroxy-3-phenylpropanoyl}oxy)-1-hydroxy-7,10-dimethoxy-9-oxo-5,20-epoxytax-11-en-2-yl benzoate.

This compound and a preparative method thereof is described in WO 96/30355, EP 0 817 779 B1 and U.S. Pat. No. 5,847,170, which are hereby incorporated herein by reference. Cabazitaxel may be administered in base form (cf. above formula), or in the form of a hydrate. It may also be a solvate, i.e. a molecular complex characterized by the incorporation of the crystallization solvent into the crystal of the molecule of the active principle (see in this respect page 1276 of J. Pharm. Sci. 1975, 64(8), 1269-1288). In particular, it may be an acetone solvate, and, more particularly, may be the solvate described in WO 2005/028462. It may be an acetone solvate of cabazitaxel containing between 5% and 8% and preferably between 5% and 7% by weight of acetone (% means content of acetone/content of acetone+cabazitaxel×100). An average value of the acetone content is 7%, which approximately represents the acetone stoichiometry, which is 6.5% for a solvate containing one molecule of acetone. The procedure described below allows the preparation of an acetone solvate of cabazitaxel:

940 ml of purified water are added at 20±5° C. (room temperature) to a solution of 207 g of 4α-acetoxy-2α-benzoyloxy-5β,20-epoxy-1β-hydroxy-7β,10β-dimethoxy-9-oxo-11-taxen-13α-yl (2R,3S)-3-tert-butoxycarbonylamino-2-hydroxy-3-phenylpropionate at about 92% by weight in about 2 litres of acetone, followed by seeding with a suspension of 2 g of 4α-acetoxy-2α-benzoyloxy-5β,20-epoxy-1β-hydroxy-7β,10β-dimethoxy-9-oxo-11-taxen-13α-yl (2R,3S)-3-tert-butoxycarbonylamino-2-hydroxy-3-phenylpropionate isolated from acetone/water in a mixture of 20 ml of water and 20 ml of acetone. The resulting mixture is stirred for about 10 to 22 hours, and 1.5 litres of purified water are added over 4 to 5 hours. This mixture is stirred for 60 to 90 minutes, and the suspension is then filtered under reduced pressure. The cake is washed on the filter with a solution prepared from 450 ml of acetone and 550 ml of purified water, and then oven-dried at 55° C. under reduced pressure (0.7 kPa) for 4 hours. 197 g of 4α-acetoxy-2α-benzoyloxy-5β,20-epoxy-1β-hydroxy-7β,10β-dimethoxy-9-oxo-11-taxen-13α-yl (2R,3S)-3-tert-butoxycarbonylamino-2-hydroxy-3-phenylpropionate acetone containing 0.1% water and 7.2% acetone (theoretical amount: 6.5% for a stoichiometric solvate) are obtained.

Cabazitaxel may be administered parenterally, such as via intravenous administration. A galenical form of cabazitaxel suitable for administration by intravenous infusion is that in which the cabazitaxel is dissolved in water in the presence of excipients chosen from surfactants, cosolvents, glucose or sodium chloride, etc. For example, a galenical form of cabazitaxel may be prepared by diluting a premix solution of cabazitaxel contained in a sterile vial (80 mg of cabazitaxel+2 ml of solvent+Polysorbate 80) with a sterile vial containing a solution of 6 ml of water and ethanol (13% by weight of 95% ethanol) in order to obtain 8 ml of a solution ready to be rediluted in a perfusion bag. The concentration of cabazitaxel in this ready-to-redilute solution is about 10 mg/ml. The perfusion is then prepared by injecting the appropriate amount of this ready-to-redilute solution into the perfusion bag containing water and glucose (about 5%) or sodium chloride (about 0.9%).

Cabazitaxel may be administered in combination with a corticoid, such as prednisone or prednisolone, as two distinct pharmaceutical preparations.

Accordingly, one aspect of the invention is a method of treating prostate cancer comprising administering to a patient in need thereof an effective amount of cabazitaxel in combination with a corticoid, such as prednisone or prednisolone.

The combination is administered repeatedly according to a protocol that depends on the patient to be treated (age, weight, treatment history, etc.), which can be determined by a skilled physician. In one aspect of the invention, cabazitaxel is administered by perfusion to the patient according to an intermittent program with an interval between each administration of 3 weeks, which may be prolonged by 1 to 2 weeks depending on the tolerance to the preceding administration. The median number of cycles is 6. The prednisone or prednisolone may be administered daily, for example in the form of one dosage intake per day, throughout the duration of the treatment. Examples of doses for the two antitumoral agents are given in the "Example" section. The currently recommended dose is 25 mg/m$^2$ of cabazitaxel administered as a on-hour infusion and 10 mg per day of prednisone or prednisolone administered orally.

In some aspects of the invention, the patient to be treated has prostate cancer that is resistant to hormone therapy (i.e., hormone refractory) and has previously been treated with docetaxel. In some aspects, the patient has prostate cancer that progressed during or after treatment with docetaxel. In some aspects, the patient was previously treated with at least 225 mg/m$^2$ cumulative dose of docetaxel. In a particular aspect, the patient showed progression of their disease in the six months following hormone therapy or during docetaxel treatment or after docetaxel treatment. In another particular aspect, the patient showed progression of their disease in the three months following hormone therapy or after docetaxel treatment.

In some aspects of the invention, the patient to be treated has a measurable tumour and may show progression of the disease via a metastatic lesion of the viscera or of a soft tissue of at least 1 cm determined by MRI or by an axial tomographic scan (CT scan).

In some aspects of the invention, the patient to be treated has an unmeasurable tumour and may show an increase in the PSA level with three measurements at a 1-week interval or the appearance of new lesions.

In some aspects of the invention, the patient to be treated has undergone castration by orchidectomy or with LHRH agonists, elimination of the androgens or monotherapy with estramustine.

In a preferred aspect, the life expectancy of the patient to be treated should be at least 2 months.

In some aspects, the treatment does not include patients who have previously received mitoxantrone, or who have received less than 225 mg/m$^2$ of docetaxel, or who have undergone a radiotherapy that has eliminated more than 40% of the marrow, who have received a treatment within the 4 weeks preceding the test, who have a neuropathy or a stomatitis, involving the brain or the meninges, who have shown severe hypersensitivity to polysorbate or to prednisone, whose blood analysis shows an appreciable decrease in neutrophils, haemoglobin or platelets, an increase in bilirubin and/or liver enzymes and creatinine, or who have heart problems or an infection requiring antibiotics.

An aspect of the invention comprises increasing the survival of a patient with hormone refractory metastatic prostate cancer, comprising administering a clinically proven effective amount of cabazitaxel to the patient in combination with prednisone or prednisolone. In a particular aspect, the patient has previously been treated with a docetaxel-containing regimen.

Cabazitaxel may be administered in combination with a medication to prevent or control nausea and vomiting or to prevent or control hypersensitivity to the cabazitaxel treatment. Preferably, a patient is pre-medicated with the medication, for example, at least 30 minutes prior to administering each dose of cabazitaxel.

One aspect of the invention comprises a method of reducing the risk of a severe hypersensitivity reaction in a patient with prostate cancer being treated with cabazitaxel, comprising administering to the patient a medication to prevent hypersensitivity prior to the administration of cabazitaxel.

Severe hypersensitivity reactions to cabazitaxel can occur and may include generalized rash/erythema, hypotension and bronchospasm. Patients should be observed closely for hypersensitivity reactions, especially during the first and second infusions. Hypersensitivity reactions may occur within a few minutes following the initiation of the infusion of cabazitaxel, thus facilities and equipment for the treatment of hypotension and bronchospasm should be available. If severe hypersensitivity reaction occurs, cabazitaxel infusion should be immediately discontinued and appropriate therapy should be administered. Examples of medications which may be used to prevent hypersensitivity to the cabazitaxel treatment include antihistamines, such as dexchlorpheniramine (for example 5 mg), and diphenhydramine (for example 25 mg) or equivalent antihistamines; and corticosteroids, such as dexamethasone (for example 8 mg) or an equivalent steroid.

Nevertheless, cabazitaxel should not be given to and may be contraindicated in patients who have a history of severe hypersensitivity reactions to cabazitaxel.

Depending on the formulation administered, cabazitaxel may also be contraindicated in patients who have a history of hypersensitivity reactions to other drugs formulated with polysorbate 80.

One aspect of the invention comprises an article of manufacture comprising:
 a) a packaging material;
 b) cabazitaxel, and
 c) a label or package insert contained within the packaging material indicating that severe hypersensitivity reactions can occur.

Gastrointestinal symptoms, such as, for example nausea, vomiting, and diarrhea, may occur with the treatment of cabazitaxel. Mortality related to diarrhea and electrolyte imbalance has been reported. Therefore, patients may also be rehydrated and treated with anti-diarrheal or anti-emetic medications as needed. Treatment delay or dosage reduction may be necessary if patients experience Grade ≥3 diarrhea.

Accordingly, the methods of the invention include administering a medication to prevent hypersensitivity or a medication to prevent or control nausea and vomiting in combination with cabazitaxel.

Examples of medications which may be used to prevent or control nausea and vomiting include histamine $H_2$ antagonists and antiemetics, such as ondansetron, granisetron and dolesetron.

A possible side effect of the treatment with cabazitaxel is neutropenia, which is characterized by a reduced number of neutrophils. Unfortunately, a number of neutropenia deaths have been reported. Therefore, frequent blood counts should be obtained or performed to monitor for neutropenia. If neutropenia occurs, cabazitaxel treatment may be discontinued, and restarted when neutrophil counts recover to a level of >1,500/mm$^3$. Cabazitaxel should not be given to a patient with a neutrophil count ≤1,500 cells/mm$^3$.

The present invention therefore also relates to a method of treating prostate cancer with cabazitaxel comprising administering cabazitaxel to the patient, monitoring blood counts in the patient, and measuring neutrophil levels. In one aspect, the method further comprises discontinuing cabazitaxel treatment if neutropenia occurs, and optionally restarting cabazitaxel treatment when neutrophil counts recover to a level of >1,500/mm$^3$. In one aspect, the monitoring comprises taking a blood sample from the patient.

Determining neutrophil counts can be performed according to procedures well know to those skilled in the art.

One aspect of the invention is a method of reducing the risk of neutropenia complications comprising administering cabazitaxel in combination with an agent useful for treating neutropenia. Such a neutropenia treatment agent is, for example, a hematopoietic growth factor which regulates the production and function of neutrophils such as a human granulocyte colony stimulating factor, (G-CSF). In a particular aspect of the invention, the neutropenia is complicated neutropenia. Complicated neutropenia includes febrile neutropenia, prolonged neutropenia, or neutropenic infection. In a preferred embodiment, the neutropenia treatment agent is administered prior to the administration of cabazitaxel.

A particular aspect of the invention comprises a method of reducing the risk of neutropenia complications in a patient with prostate cancer being treated with cabazitaxel, comprising monitoring blood counts in the patient at regular intervals during treatment of the patient with cabazitaxel; reducing the dose of cabazitaxel if the patient experiences febrile neutropenia or prolonged neutropenia; discontinuing cabazitaxel treatment if the patients neutrophil count is ≤1,500 cells/mm$^3$; and optionally restarting cabazitaxel treatment when the patients neutrophil counts recover to a level ≤1,500 cells/mm$^3$.

In a particular aspect, primary prophylaxis with G-CSF should be considered in patients with high-risk clinical features (age >65 years, poor performance status, previous episodes of febrile neutropenia, extensive prior radiation ports, poor nutritional status, or other serious co-morbidities) that predispose them to increased complications from prolonged neutropenia. Therapeutic use of G-CSF and secondary prophylaxis should be considered in all patients considered to be at increased risk for neutropenia complications.

In another aspect, the monitoring of complete blood counts is performed on a weekly basis during cycle 1 and before each treatment cycle thereafter so that the dose can be adjusted, if needed. Therefore, another aspect for reducing the risk of neutropenia complications comprises monitoring blood counts in the patient and adjusting the dose of cabazitaxel. An example of a dose modification is described in Example 2.

One aspect of the invention comprises an article of manufacture comprising:
 a) a packaging material;
 b) cabazitaxel, and
 c) a label or package insert contained within the packaging material indicating that cabazitaxel should not be given to patients with neutrophil counts of s1,500 cells/mm$^3$.

Cases of renal failure should be indentified and managed aggressively, accordingly to procedures known to those skilled in the art. Renal failure may be associated with sepsis, dehydration, or obstructive uropathy. Furthermore, impaired hepatic function (e.g., total bilirubin ≥ULN, or AST and/or ALT ≥1.5×ULN) may increase cabazitaxel concentrations, and cabazitaxel should not be given to patients with hepatic impairment.

Cabazitaxel may cause fetal harm when administered to a pregnant woman.

Prednisone or prednisolone administered at 10 mg daily does not affect the pharmacokinetics of cabazitaxel.

Cabazitaxel is primarily metabolized through CYP3A. Concomitant administration of strong CYP3A inhibitors (for example, ketoconazole, itraconazole, clarithromycin, atazanavir, indinavir, nefazodone, nelfinavir, ritonavir, saquinavir, telithromycin, voriconazole) may increase cabazitaxel concentrations. Therefore co-administration of cabazitaxel with strong CYP3A inhibitors should be avoided. Caution should be exercised with concomitant use of moderate CYP3A inhibitors. One aspect of the invention is a method of treating a patient for prostate cancer comprising determining whether the patient is undergoing treatment with a CYP3A inhibitor, discontinuing treatment with a CYP3A inhibitor, and then administering cabazitaxel to the patient.

Concomitant administration of strong CYP3A inducer (e.g., phenytoin, carbamazepine, rifampin, rifabutin, rifapentin, phenobarbital) may decrease cabazitaxel concentrations. Therefore co-administration of cabazitaxel with strong CYP3A inducers should be avoided. Therefore, one aspect of the invention is a method of treating a patient for prostate cancer comprising determining whether the patient is undergoing treatment with a CYP3A inducer, discontinuing treatment with a CYP3A inducer, and administering cabazitaxel to the patient.

In addition, patients should also refrain from taking St. John's Wort.

In some aspects of the invention, the cabazitaxel is administered in an amount to provide an AUC of about 991 ng·h/mL (CV 34%).

In some aspects of the invention, the cabazitaxel is administered in an amount to provide an $C_{max}$ of about 226 ng·h/mL (CV 107%).

In some aspects of the invention, the cabazitaxel is administered in an amount to provide a plasma clearance of 48.5 L/h (CV 39%).

One aspect of the invention is a package comprising cabazitaxel and a label, in a position which is visible to prospective purchasers, comprising a printed statement which informs prospective purchasers that the mean $C_{max}$ of cabazitaxel in patients with metastatic prostate cancer was 226 ng/mL (CV 107%).

Another aspect of the invention is a package comprising cabazitaxel and a label, in a position which is visible to prospective purchasers, comprising a printed statement which informs prospective purchasers that the mean AUC of cabazitaxel in patients with metastatic prostate cancer was 991 ng·h/mL (CV 34%).

Another aspect of the invention is a package comprising cabazitaxel and a label, in a position which is visible to prospective purchasers, comprising a printed statement which informs prospective purchasers that cabazitaxel has a plasma clearance of 48.5 L/h (CV 39%).

A variety of educational materials may be employed to ensure proper prescribing, dispensing, and patient compliance according to the methods described herein. For example, a variety of literature and other materials, such as, for example, prescribing information, package inserts, medications guides, physician information sheets, healthcare professional information sheets, medical journal advertisements, and product websites may describe the risks and benefits of taking cabazitaxel.

The invention also concerns a package comprising cabazitaxel and a label, said label comprising one or more messages that:
a) the efficacy and safety of cabazitaxel in combination with prednisone were evaluated in patients with hormone refractory metastatic prostate cancer previously treated with a docetaxel containing regimen; or
b) a total of 755 patients were randomized to receive either cabazitaxel 25 mg/m³ every 3 weeks for a maximum of 10 cycles with prednisone mg orally daily, or to receive mitoxantrone 12 mg/m² intravenously every 3 weeks for a maximum of 10 cycles with prednisone 10 mg orally daily; or
c) the median number of cycles was 6 in the cabazitaxel group and 4 in the mitoxantrone group.

The invention also concerns a package comprising cabazitaxel and a label, said label comprising one or more messages that:
a) neutropenic deaths have been reported; or
b) frequent blood counts should be obtained to monitor for neutropenia; or
c) cabazitaxel should not be given if neutrophil counts are ≤1,500 cells/mm³.

The invention also concerns a method of promoting the use of cabazitaxel the method comprising the step of conveying to a recipient at least one message selected from:
a) neutropenic deaths have been reported; or
b) frequent blood counts should be obtained to monitor for neutropenia; or
c) cabazitaxel should not be given if neutrophil counts are ≤1,500 cells/mm³;
d) severe hypersensitivity can occur; or
e) severe hypersensitivity can occur and may include generalized rash/erythema, hypotension and brochospasm; or
f) discontinue cabazitaxel immediately if severe reactions occur; or
g) discontinue cabazitaxel immediately if severe reactions occur and administer appropriate therapy; or
h) cabazitaxel is contraindicated in patients with a history of severe hypersensitivity reactions to cabazitaxel or drugs formulated with polysorbate 80.

The invention also concerns a method of providing cabazitaxel, wherein said cabazitaxel is provided along with information indicating that:
a) neutropenic deaths have been reported; or
b) frequent blood counts should be obtained to monitor for neutropenia; or
c) cabazitaxel should not be given if neutrophil counts are ≤1,500 cells/mm³;
d) severe hypersensitivity can occur or
e) severe hypersensitivity can occur and may include generalized rash/erythema, hypotension and brochospasm; or
f) discontinue cabazitaxel immediately if severe reactions occur, or
g) discontinue cabazitaxel immediately if severe reactions occur and administer appropriate therapy; or
h) cabazitaxel is contraindicated in patients with a history of severe hypersensitivity reactions to cabazitaxel or drugs formulated with polysorbate 80.

Example 1

A clinical study was performed wherein patients received either treatment with cabazitaxel or the reference treatment based on mitoxantrone each combined with prednisone or prednisolone.

More specifically, patients over 18 years of age with metastatic castration resistant metastatic prostate cancer either measurable by RECIST criteria or non-measurable disease with rising PSA levels or appearance of new lesions, ECOG (Eastern Cooperative Oncology Group) performance stage 0-2, and adequate organ function (patients had to have neutrophils ≥1,500 cells/mm³, platelets >100,000 cells/mm³, hemoglobin >10 g/dL, creatinine <1.5×upper limit of normal (ULN), total bilirubin <1×ULN, AST <1.5×ULN, and ALT <1.5×ULN) who had had prior hormone therapy, chemotherapy, and radiotherapy, but had progressive during or after docetaxel treatment (cumulative dose ≥225 mg/m²) were randomized to 10 mg/day of prednisone with either mitoxantrone 12 mg/m² or cabazitaxel 25 mg/m², both administered every 3 weeks.

Patients with a history of congestive heart failure, or myocardial infarction within the last 6 months, or patients with uncontrolled cardiac arrhythmias, angina pectoris, and/or hypertension were not included in the study.

720 patients were planned to be included in the clinical study: 360 in each cabazitaxel+prednisone and mitoxantrone+prednisone group. Seven hundred and fifty-five patients (755) (median age 68; 84% white) were actually enrolled, 378 in the cabazitaxel and prednisone/prednisolone group and 377 in the mitoxantrone and prednisone/prednisolone group. The maximal number of treatment cycles was 10 for cabazitaxel and 10 for mitoxantrone. The median number of treatment cycles was 6 for cabazitaxel and 4 for mitoxantrone. The median prior dose of docetaxel treatment was 576 mg/m$^2$ for the cabazitaxel group and 529 mg/m$^2$ for the mitoxantrone group. Median follow-up was 12.8 months.

The measurements of the results are performed via the same tests as at inclusion. MRI and spiral computed tomographic (CT) scans are preferably used.

The results are evaluated according to the following criteria (cf RECIST guideline):
  overall survival (OS): the time from inclusion to the study to the date of death complete response (CR): disappearance of the lesions
  partial response (PR): at least 30% reduction of the largest diameter of the lesion progression (PD): at least 20% increase in the sum of the largest diameter of the lesion or appearance of one or more new lesions
  stable disease (SD): reduction of the tumour insufficient to be included in PR and increase of the tumour insufficient to be included in PD.

The confirmations of the measurements are made at least 4 weeks after the response criterion has been established for the first time.

The progression-free survival (PFS) is the time from inclusion in the study and the date of progression or death when the progression is either an increase of the PSA, or of the tumour, or of the pain.

It was found that the combination of cabazitaxel and prednisone is a well-tolerated combination with the safety profile of taxanes. At the dose investigated in this trial (LD2: 25 mg/m$^2$ cabazitaxel+10 mg/m$^2$/day prednisone), patients receiving cabazitaxel demonstrated statistically significant longer overall survival (OS) compared to mitoxantrone (p<0.0001). The hazard ratio was 0.70 (95% CI. 0.59, 0.83) in favor of cabazitaxel corresponding to a 30% reduction in risk of death. The median survival for patients in the cabazitaxel group was 15.1 months in comparison to 12.7 months in the mitoxantrone group. Notably, the extension of survival was observed irrespective of ECOG performance status, number of prior chemotherapy regimens and age. Benefit was also seen in the third of patients who were docetaxel-refractory and had progressed during docetaxel therapy.

The data related to the treated patients are given in Table 1:

TABLE 1

| Efficacy analysis (intention-to-treat) | | | |
|---|---|---|---|
| | | CbzP N = 378 Median (months) | MP N = 377 Median (months) |
| Overall survival | Median (months) | 15.1 | 12.7 |
| | Hazard ratio (95% CI) | 0.70 (0.59; 0.83) | |
| | p-value[1] | 0.0001 | |

TABLE 1-continued

| Efficacy analysis (intention-to-treat) | | | |
|---|---|---|---|
| | | CbzP N = 378 Median (months) | MP N = 377 Median (months) |
| PFS | Median (months) | 2.8 | 1.4 |
| | Hazard ratio (95% CI) | 0.74 (0.64-0.86) | |
| | p-value[1] | 0.0001 | |
| | Tumor response rate | 14.4% | 4.4% |
| | p-value[2] | 0.0005 | |
| Time to Tumor Progression Median (months) | | 8.8 | 5.4 |
| | p-value | <0.001 | |
| | PSA Response rate | 39.2% | 17.8% |
| | p-value[2] | 0.0002 | |
| PSA PFS | Median (months) | 6.4 | 3.1 |
| | Hazard ratio (95% CI) | 0.75 (0.63-0.90) | |
| | p-value[1] | 0.0010 | |
| | Pain Response rate | 9.2% | 7.8% |
| | p-value[2] | 0.6526 | |
| Pain PFS | Median (months) | Not reached | 11.1 |
| | Hazard ratio (95% CI) | 0.91 (0.69-1.19) | |
| | p-value[1] | 0.5192 | |

[1]Log-rank test;
[2]Chi-square test
CbzP: cabazitaxel with prednisone
MP: mitoxantrone with prednisone Progression free survival (PFS) defined as the earliest progression in tumor, PSA or pain was also statistically significantly longer in the cabazitaxel group compared to the mitoxantrone group (p<0.0001, hazard ratio=0.74 (95% CI, 0.64, 0.86), and the median progression-free survival was 2.8 months versus 1.4 months. Response rates and PFS for PSA and tumor assessments were statistically significant in favor of cabazitaxel, while response rate and PFS for pain did not show a statistically significant difference.

The most frequent Grade 3/4 toxicities were neutropenia observed with a higher frequency in the cabazitaxel group with 81.7% compared to the mitoxantrone group with 58.0%. Rates of febrile neutropenia were 7.5% in the cabazitaxel group and 1.3% in the mitoxantrone group.

The most common (≥20%) grade 1-4 adverse reactions were anemia, leukopenia, neutropenia, thrombocytopenia, diarrhea, fatigue, nausea, vomiting, asthenia, and constipation.

The most common (≥5%) grade 3-4 adverse reactions in patients who received cabazitaxel were neutropenia, leukopenia, anemia, febrile neutropenia, diarrhea, fatigue, and asthenia.

Subgroup analyses by risk factors and a multivariate analysis showed that OS outcomes were consistent and robust in favor of cabazitaxel as shown in the herebelow table:

TABLE 2

| | MP | | CbzP | | |
|---|---|---|---|---|---|
| | N (%) | Median OS (mos) | N (%) | Median OS (mos) | CbzP vs MP HR (95% CI) |
| ITT | 377 (100) | 12.7 | 378 (100) | 15.1 | 0.70 (0.59-0.83) |
| PD while on D | 103 (27) | 12.0 | 113 (30) | 14.2 | 0.65 (0.47-0.90) |

TABLE 2-continued

|  | MP | | CbzP | | |
|---|---|---|---|---|---|
|  | N (%) | Median OS (mos) | N (%) | Median OS (mos) | CbzP vs MP HR (95% CI) |
| PD after last D dose, ≤3 mos | 180 (48) | 10.3 | 158 (42) | 13.9 | 0.70 (0.54-0.90) |
| PD after last D dose, >3 mos | 91 (24) | 17.7 | 103 (27) | 17.5 | 0.78 (0.53-1.14) | mos = months
0 = Docetaxel

TABLE 3

Incidence of Reported Adverse Reactions[1] and Hematologic Abnormalities in ≥5% of Patients Receiving cabazitaxel in Combination with Prednisone or Mitoxantrone in Combination with Prednisone

|  | Cabazitaxel 25 mg/m² every 3 weeks with prednisone 10 mg daily n = 371 | | Mitoxantrone 12 mg/m² every 3 weeks with prednisone 10 mg daily n = 371 | |
|---|---|---|---|---|
| Any Adverse Reaction | Grade 1-4 n (%) | Grade 3-4 n (%) | Grade 1-4 n (%) | Grade 3-4 n (%) |
| Blood and Lymphatic System Disorders | | | | |
| Neutropenia[2] | 347 (94%) | 303 (82%) | 325 (87%) | 215 (58%) |
| Febrile Neutropenia | 27 (7%) | 27 (7%) | 5 (1%) | 5 (1%) |
| Anemia[2] | 361 (98%) | 39 (11%) | 302 (82%) | 18 (5%) |
| Leukopenia[2] | 355 (96%) | 253 (69%) | 343 (93%) | 157 (42%) |
| Thrombocytopenia[2] | 176 (48%) | 15 (4%) | 160 (43%) | 6 (2%) |
| Cardiac Disorders | | | | |
| Arrhythmia[3] | 18 (5%) | 4 (1%) | 6 (2%) | 1 (<1%) |
| Gastrointestinal Disorders | | | | |
| Diarrhea | 173 (47%) | 23 (6%) | 39 (11%) | 1 (<1%) |
| Nausea | 127 (34%) | 7 (2%) | 85 (23%) | 1 (<1%) |
| Vomiting | 83 (22%) | 6 (2%) | 38 (10%) | 0 |
| Constipation | 76 (20%) | 4 (1%) | 57 (15%) | 2 (<1%) |
| Abdominal Pain[4] | 64 (17%) | 7 (2%) | 23 (6%) | 0 |
| Dyspepsia[5] | 36 (10%) | 0 | 9 (2%) | 0 |
| General Disorders and Administration Site Conditions | | | | |
| Fatigue | 136 (37%) | 18 (5%) | 102 (27%) | 11 (3%) |
| Asthenia | 76 (20%) | 17 (5%) | 46 (12%) | 9 (2%) |
| Pyrexia | 45 (12%) | 4 (1%) | 23 (6%) | 1 (<1%) |
| Peripheral Edema | 34 (9%) | 2 (<1%) | 34 (9%) | 2 (<1%) |
| Mucosal Inflammation | 22 (6%) | 1 (<1%) | 10 (3%) | 1 (<1%) |
| Pain | 20 (5%) | 4 (1%) | 18 (5%) | 7 (2%) |
| Infections and Infestations | | | | |
| Urinary Tract Infection[6] | 29 (8%) | 6 (2%) | 12 (3%) | 4 (1%) |
| Pneumonia[7] | 12 (3%) | 9 (2%) | 4 (1%) | 3 (<1%) |
| Investigations | | | | |
| Weight Decreased | 32 (9%) | 0 | 28 (8%) | 1 (<1%) |
| Metabolism and Nutrition Disorders | | | | |
| Anorexia | 59 (16%) | 3 (<1%) | 39 (11%) | 3 (<1%) |
| Dehydration | 18 (5%) | 8 (2%) | 10 (3%) | 3 (<1%) |
| Musculoskeletal and Connective Tissue Disorders | | | | |
| Back Pain | 60 (16%) | 14 (4%) | 45 (12%) | 11 (3%) |
| Arthralgia | 39 (11%) | 4 (1%) | 31 (8%) | 4 (1%) |
| Pain in Extremity | 30 (8%) | 6 (2%) | 27 (7%) | 4 (1%) |
| Muscle Spasms | 27 (7%) | 0 | 10 (3%) | 0 |
| Bone Pain | 19 (5%) | 3 (<1%) | 19 (5%) | 9 (2%) |
| Musculoskeletal Pain | 18 (5%) | 2 (<1%) | 20 (5%) | 3 (<1%) |
| Nervous System Disorders | | | | |
| Peripheral Neuropathy[8] | 50 (13%) | 3 (<1%) | 12 (3.2%) | 3 (<1%) |
| Dysgeusia | 41 (11%) | 0 | 15 (4%) | 0 |
| Dizziness | 30 (8%) | 0 | 21 (6%) | 2 (<1%) |
| Headache | 28 (8%) | 0 | 19 (5%) | 0 |
| Renal and Urinary Tract Disorders | | | | |
| Hematuria | 62 (17%) | 7 (2%) | 13 (4%) | 1 (<1%) |
| Dysuria | 25 (7%) | 0 | 5 (1%) | 0 |
| Respiratory, Thoracic and Mediastinal Disorders | | | | |
| Dyspnea | 43 (12%) | 4 (1%) | 16 (4%) | 2 (<1%) |
| Cough | 40 (11%) | 0 | 22 (6%) | 0 |
| Skin and Subcutaneous Tissue Disorders | | | | |
| Alopecia | 37 (10%) | 0 | 18 (5%) | 0 |
| Vascular Disorders | | | | |
| Hypotension | 20 (5%) | 2 (<1%) | 9 (2%) | 1 (<1%) |
| Median Duration of Treatment | 6 cycles | | 4 cycles | |

[1]Graded using NCI CTCAE version 3
[2]Based on laboratory values, cabazitaxel: n = 369, mitoxantrone: n = 370.
3Includes atrial fibrillation, atrial flutter, atrial tachycardia, atrioventricular block complete, bradycardia, palpitations, supraventricular tachycardia, tachyarrhythmia, and tachycardia.
[4]Includes abdominal discomfort, abdominal pain lower, abdominal pain upper, abdominal tenderness, and GI pain.
[5]Includes gastroesophageal reflux disease and reflux gastritis.
[6]Includes urinary tract infection enterococcal and urinary tract infection fungal.
[7]Includes bronchopneumonia, lobar pneumonia, and pneumonia klebsiella.
[8]Includes peripheral motor neuropathy and peripheral sensory neuropathy.

TABLE 4

Patient Characteristics

|  | MP (n = 377) | CBZP (n = 378) |
|---|---|---|
| Age (years) | | |
| Median [range] | 67 [47-89] | 68 [46-92] |
| ≥65 (%) | 57.0 | 64.9 |
| ECOG PS (%) | | |
| 0, 1 | 91.2 | 92.6 |
| 2 | 8.8 | 7.4 |
| PSA* (ng/mL) | | |
| Median [range] | 127.5 [2-11220] | 143.9 [2-7842] |
| Measurability of disease (%) | | |
| Measurable | 54.1 | 53.2 |
| Nonmeasurable | 45.9 | 46.8 |
| Disease site (%) | | |
| Bone | 87.0 | 80.2 |
| Lymph node | 44.8 | 45.0 |
| Visceral | 24.9 | 24.9 |
| Pain at Baseline, no. (%) | 168 (44.6) | 174 (46.0) |
| Previous Therapy, no. (%) | | |
| Hormonal | 375 (99.5) | 375 (99.2) |
| No. of Chemotherapy | | |

TABLE 4-continued

Patient Characteristics

| | MP (n = 377) | CBZP (n = 378) |
|---|---|---|
| Regimens | | |
| 1 | 268 (71.1) | 260 (68.8) |
| 2 | 79 (21.0) | 94 (24.9) |
| >2 | 30 (8.0) | 24 (6.3) |
| Radiation | 222 (58.9) | 232 (61.4) |
| Surgery | 205 (54.4) | 198 (52.4) |
| Biologic Agent | 36 (9.5) | 26 (6.9) |
| Previous docetaxel regimens, n (%) | | |
| 1 | 327 (86.7) | 316 (83.6) |
| 2 | 43 (11.4) | 53 (14.0) |
| >2 | 7 (1.9) | 9 (2.4) |
| Median total previous docetaxel dose (mg/m$^2$) | 529.2 | 576.6 |
| Disease progression relative to docetaxel administration, n (%) | | |
| During treatment | 104 (27.6) | 115 (30.4) |
| <3 months from last dose | 181 (48.0) | 158 (41.8) |
| ≥3 months from last dose | 90 (23.9) | 102 (27.0) |
| Unknown | 2 (0.5) | 3 (0.8) |
| Median time from last docetaxel dose to disease progression (months) | 0.7 | 0.8 |

The primary reason for treatment discontinuation in both groups was disease progression (Table 5). The median delivered relative dose intensity was 96.1% in the cabazitaxel group and 97.3% in the mitoxantrone group. In the cabazitaxel group, >75% of patients received >90% of the planned dose intensity. Overall, 5.1% of mitoxantrone treatment courses were dose reduced compared with 9.8% of cabazitaxel treatment courses; 6.3 and 7% of all treatment courses were delayed by 9 days or less, and 1.6 and 2.3% of courses were delayed by more than 9 days for mitoxantrone and cabazitaxel respectively (See Table 5).

TABLE 5

Treatment Received and Reasons for Discontinuation in the Intention-to-Treat Population.*

| | Mitoxantrone (N = 377) | Cabazitaxel (N = 378) |
|---|---|---|
| Patients receiving study treatment, no. (%) | 371 (98.4) | 371 (98.1) |
| Patients completing planned ten cycles of study treatment, no. (%) | 46 (12.2) | 105 (27.8) |
| Discontinuation of study treatment, no. (%) | 325 (86.2) | 266 (70.4) |
| Reasons for discontinuation of study treatment, no. (%) | | |
| Disease progression | 267 (70.8) | 180 (47.6) |
| Adverse event | 32 (8.5) | 67 (17.7) |
| Non-compliance with protocol | 0 | 1 (0.3) |
| Lost to follow-up | 2 (0.5) | 0 |
| Patient's request | 17 (4.5) | 8 (2.1) |
| Other | 7 (1.9) | 10 (2.7) |
| No. of treatment cycles, median (range)† | 4 (1-10) | 6 (1-10) |
| Relative dose intensity, median % (range)† | 97.3 (42.5-106.0) | 96.1 (49.0-108.2) |
| Treatment delays, no. of cycles (%)‡ | | |
| ≤9 days | 110 (6.3) | 157 (7.0) |

TABLE 5-continued

Treatment Received and Reasons for Discontinuation in the Intention-to-Treat Population.*

| | Mitoxantrone (N = 377) | Cabazitaxel (N = 378) |
|---|---|---|
| >9 days | 28 (1.6) | 51 (2.3) |
| Dose reductions, no. of cycles (%)‡ | 88 (5.1) | 221 (9.8) |

Figure 2:
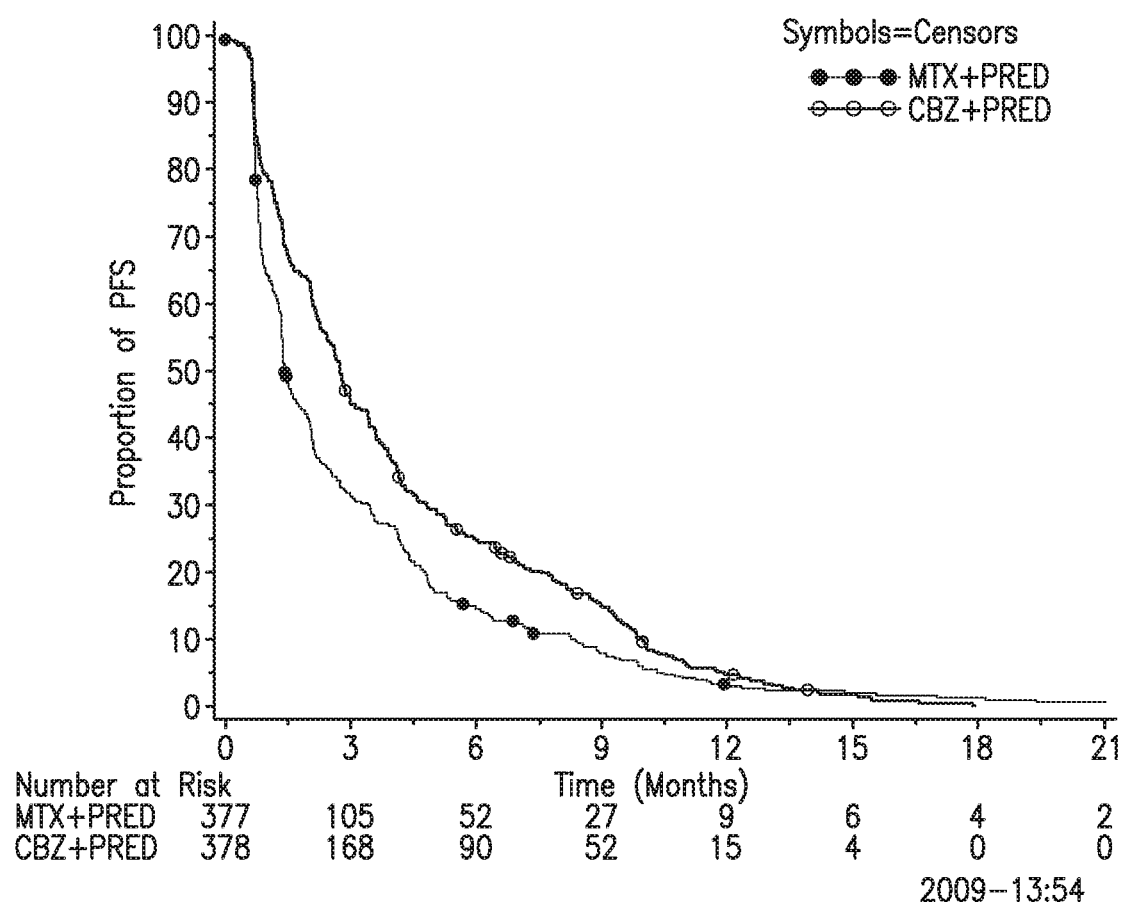
FIG. 2 displays the Kaplan-Meier curves of progression-free survival in a cabazitaxel study.
Figure 3:
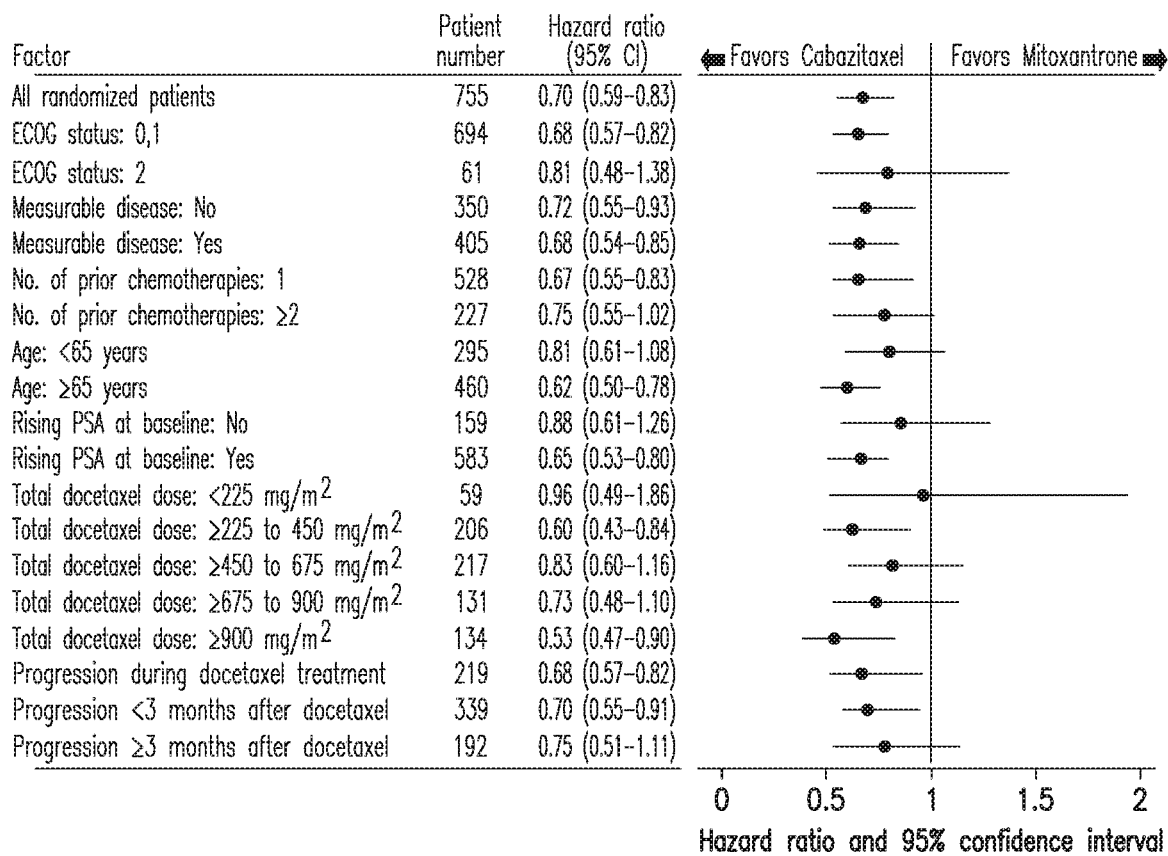
FIG. 3 shows an intention-to-treat analysis of overall survival in subgroups of patients defined by baseline characteristics. Hazard ratios <1 favor the cabazitaxel group, while those >1 favor the mitoxantrone group. CI denotes confidence intervals.

The results of this study are further illustrated to FIGS. 1, 2, and 3.

Example 2

Table 6 illustrates an example of a dosage modification for adverse reactions in patients treated with cabazitaxel

TABLE 6

| Toxicity | Dosage Modification |
|---|---|
| Prolonged grade ≥3 neutropenia greater than 1 week) despite appropriate medication including G-CSF | Delay treatment until neutrophil count is >1,500 cells/mm$^3$, then reduce dosage of cabazitaxel to 20 mg/m$^2$. Use G-CSF for secondary prophylaxis. |
| Febrile neutropenia | Delay treatment until improvement or resolution, and until neutrophil count is >1,500 cells/mm$^3$, then reduce dosage of cabazitaxel to 20 mg/m$^2$. Use G-CSF for secondary prophylaxis. |
| Grade >3 diarrhea or persisting diarrhea despite appropriate medication, fluid and electrolytes replacement | Delay treatment until improvement or resolution, then reduce dosage of cabazitaxel to 20 mg/m$^2$. |

Discontinue cabazitaxel treatment if a patient continues to experience any of these reactions at 20 mg/m$^2$.

Example 3

Figure 4:
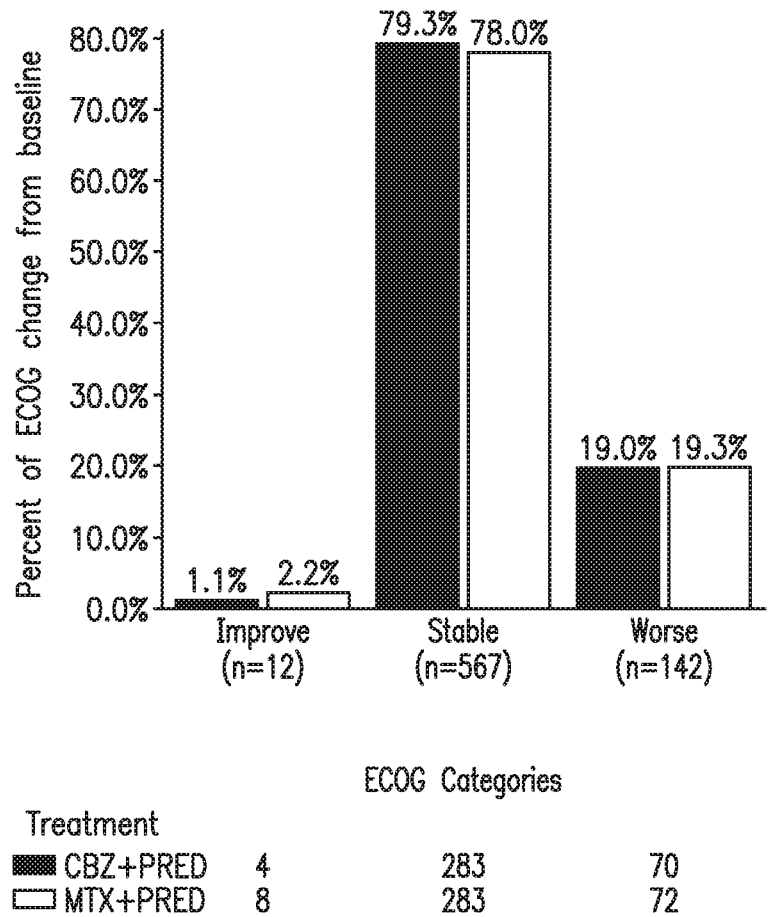
FIG. 4 graphically depicts the proportion of patients with changes in ECOG performance status from baseline during treatment (safety population). The "Improved" column represents PS2 at baseline changed to 0 or 1 during treatment. The "stable" column represents no change, and the "Worse" column represents PS2 at baseline and changed to ≥3, or 0 or 1 at baseline changed to ≥2 during treatment.
Figure 5:
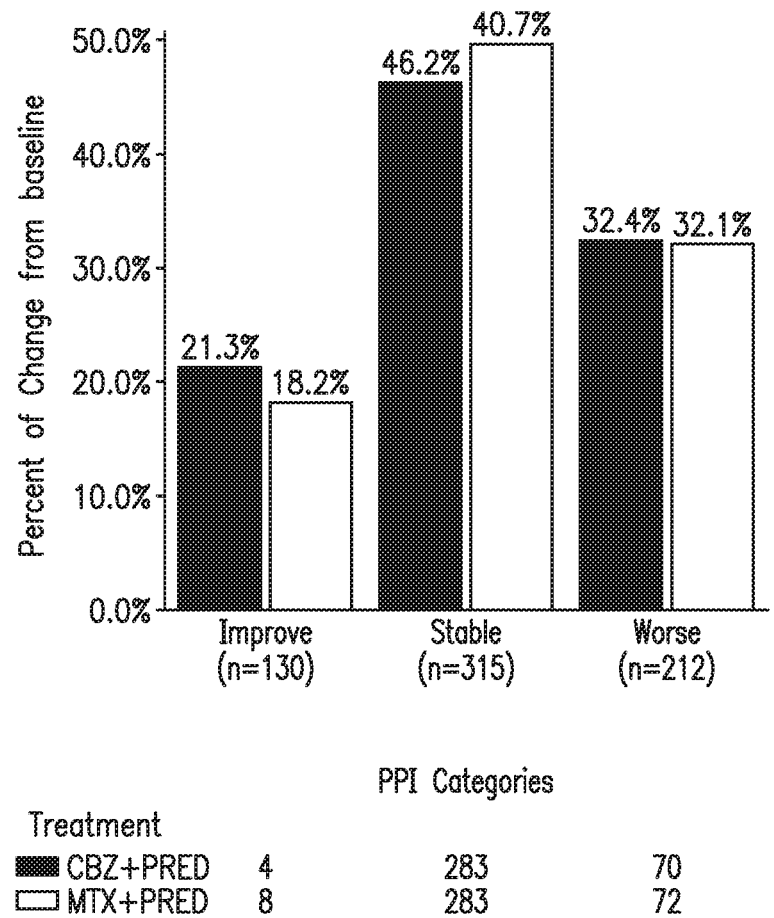
FIG. 5 graphically depicts the proportion of patients with changes from baseline in the Present Pain Intensity score during treatment (ITT). The "Improved" column represents patients in which the PPI score during treatment was lower versus baseline. The "Stable" column represents no change, and the "Worse" column represents patients with >1 unit increase in PPI score during treatment versus baseline.
Figure 6:
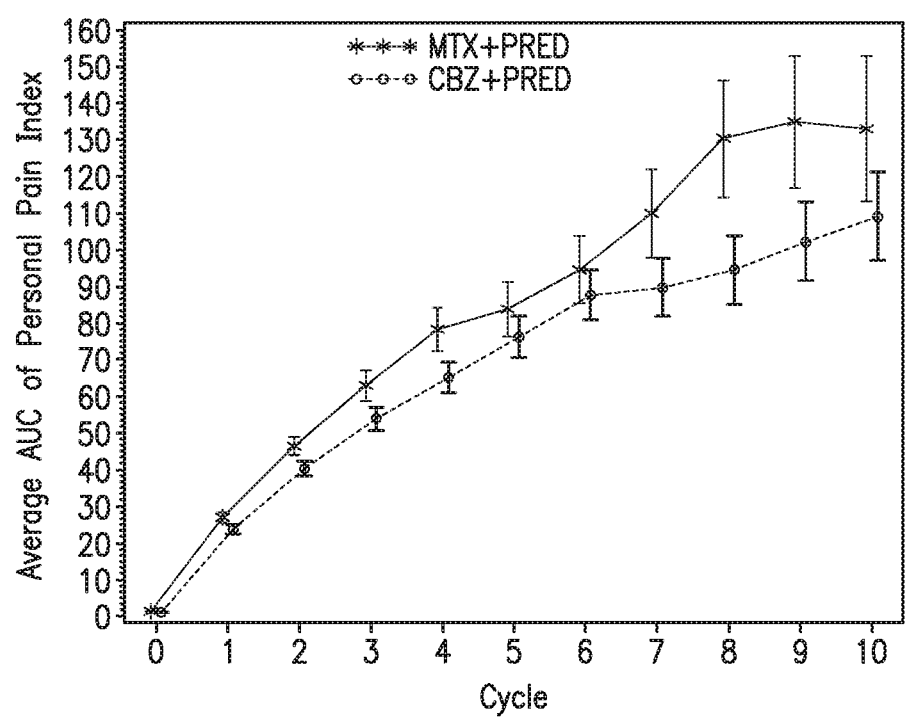
FIG. 6 graphically presents the mean area under the curve for PPI and analgesic scores by treatment cycle.

Performance Status and Pain Scores During Treatment
Methods
 ECOG PS, pain measures, and analgesic consumption were assessed prior to every treatment cycle and at the end of study treatment.
 Pain assessments: Present Pain Intensity (PPI) scale from the McGill-Melzack questionnaire (Melzack R. Pain 1975; 1:277-99). Mean Analgesic Score (AS) derived from analgesic consumption (in morphine equivalents) was calculated for the one-week period prior to each evaluation. Area under the curve (AUC) of PPI and AS was calculated by the trapezoid formula. Cumulative AUC of PPI and AS was calculated up to the last cycle of data available for each patient. Average AUC of the treatment groups was compared from Cycle 1 to Cycle 10.
Results
 Performance status remained stable in most patients during the treatment period and was similar between groups. See FIG. 4.
 Overall, PPI scores were comparable; improving from baseline in 21.3% of men in the CbzP group and 18.2% in the MP group. See FIG. 5.
 The CbzP group had a lower mean area under the curve (AUC) of PPI, suggesting less severe pain especially during cycles 7-10. See FIG. 6.

Figure 7:
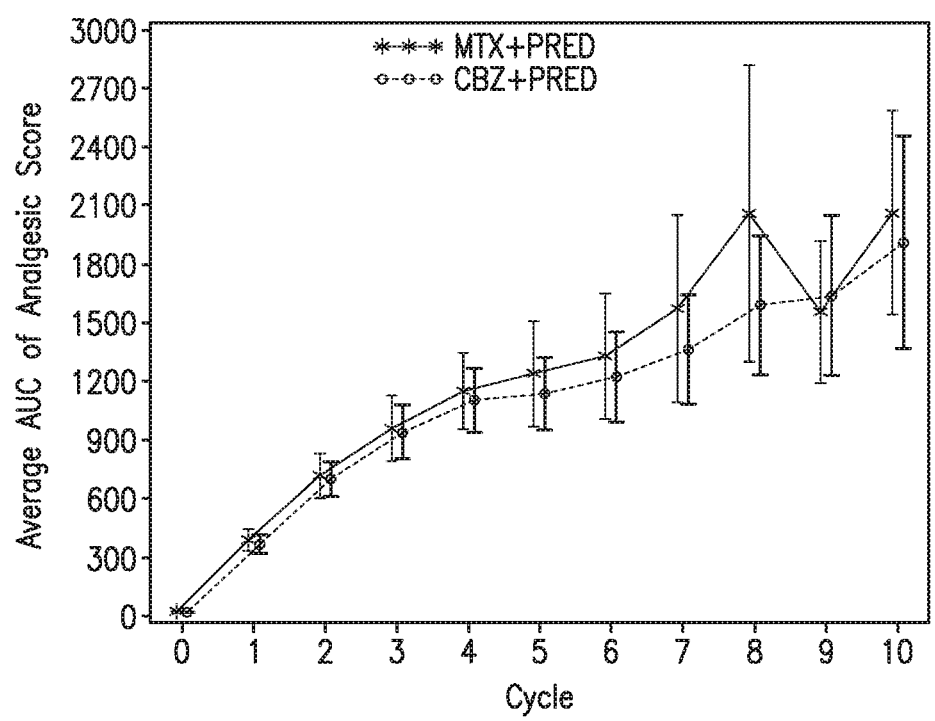
FIG. 7 graphically presents the mean AUC analgesic score.

Analgesic use was comparable between the groups (lower mean AUC of AS means lower pain medication use). See FIG. 7.

CONCLUSION

Despite longer treatment with CbzP no worsening in ECOG PS was seen.

Present Pain Intensity score improved in 21% of men in CbzP vs. 18% in MP arm.

Assessment of pain scores suggested less severe pain in the CbzP group during treatment.

Pain medication use was similar between groups.

Example 4

A population pharmacokinetic analysis was conducted in 170 patients with solid tumors at doses ranging from 10 to 30 mg/m² weekly or every 3 weeks.

Based on the population pharmacokinetic analysis, after an intravenous dose of cabazitaxel 25 mg/m² every 3 weeks, the mean $C_{max}$ in patients with metastatic prostate cancer was 226 ng/mL (CV 107%) and was reached at the end of the 1-hour infusion ($T_{max}$). The mean AUC in patients with metastatic prostate cancer was 991 ng·h/mL (CV 34%). No major deviation from the dose proportionality was observed from 10 to 30 mg/m² in patients with advanced solid tumors. The volume of distribution (Vss) was 4,864 L (2,643 L/m² for a patient with a median BSA of 1.84 m²) at steady state.

Based on the population pharmacokinetic analysis, cabazitaxel has a plasma clearance of 48.5 L/h (CV 39%; 26.4 L/h/m² for a patient with a median BSA of 1.84 m²) in patients with metastatic prostate cancer. Following a 1-hour intravenous infusion, plasma concentrations of cabazitaxel can be described by a 3-compartment PK model with α-, β-, and γ-half-lives of 4 minutes, 2 hours, and 95 hours, respectively.

What is claimed is:

1. A method of increasing survival comprising administering to a patient in need thereof (1) cabazitaxel, or a hydrate of solvate thereof, as a new cycle every three weeks and (2) dexchlorpheniramine administered at a dose of 5 mg, dexamethasone administered at a dose of 8 mg, and an H2 antagonist, each administered prior to the administration of said cabazitaxel, or hydrate of solvate thereof, wherein said patient has castration resistant metastatic prostate cancer that has progressed during or after treatment with docetaxel.

2. The method according to claim 1, wherein the dexchlorpheniramine, dexamethasone, and H2 antagonist are administered 30 minutes prior to the administration of said cabazitaxel, or hydrate of solvate thereof.

3. The method according to claim 2, wherein the dose of said cabazitaxel, or hydrate or solvate thereof, is 15-25 mg/m².

4. The method according to claim 3, wherein the dose of said cabazitaxel, or hydrate or solvate thereof, is 25 mg/m².

5. The method according to claim 3, wherein the dose of said cabazitaxel, or hydrate or solvate thereof, is 20 mg/m².

6. The method according to claim 3, wherein the dose of said cabazitaxel, or hydrate or solvate thereof, is 15 mg/m².

* * * * *